US012410184B2

(12) United States Patent
Bakale et al.

(10) Patent No.: US 12,410,184 B2
(45) Date of Patent: Sep. 9, 2025

(54) CRYSTALLINE FORMS OF A MENIN INHIBITOR

(71) Applicant: Kura Oncology, Inc., San Diego, CA (US)

(72) Inventors: Roger Paul Bakale, San Diego, CA (US); Craig Michael Bowe, San Diego, CA (US); Dipanjan Sengupta, San Diego, CA (US); Patricia Andres, Bend, OR (US); Xiaohu Deng, San Diego, CA (US)

(73) Assignee: Kura Oncology, Inc., San Diego, CA (US)

( * ) Notice: Subject to any disclaimer, the term of this patent is extended or adjusted under 35 U.S.C. 154(b) by 0 days.

(21) Appl. No.: 18/827,512

(22) Filed: Sep. 6, 2024

(65) Prior Publication Data

US 2025/0101035 A1 Mar. 27, 2025

Related U.S. Application Data

(63) Continuation of application No. PCT/US2024/038216, filed on Jul. 16, 2024.

(60) Provisional application No. 63/655,384, filed on Jun. 3, 2024, provisional application No. 63/514,089, filed on Jul. 17, 2023.

(51) Int. Cl.
*C07D 495/04* (2006.01)

(52) U.S. Cl.
CPC .................. *C07D 495/04* (2013.01)

(58) Field of Classification Search
CPC .................................................. C07D 495/04
See application file for complete search history.

(56) References Cited

U.S. PATENT DOCUMENTS

| 4,432,987 | A | * | 2/1984 | Barth ...................... A61P 31/04 |
| | | | | 514/193 |
| 10,077,271 | B2 | | 9/2018 | Grembecka et al. |
| 10,174,041 | B2 | | 1/2019 | Grembecka et al. |
| 10,781,218 | B2 | | 9/2020 | Wu et al. |
| 11,396,517 | B1 | * | 7/2022 | Dai ......................... A61P 35/00 |
| 11,673,898 | B2 | | 6/2023 | Wu et al. |
| 2025/0099469 | A1 | * | 3/2025 | Tao .......................... A61P 35/00 |

FOREIGN PATENT DOCUMENTS

| WO | WO-2016195776 A1 | 12/2016 |
| WO | WO-2017161028 A1 | 9/2017 |
| WO | WO-2018106820 A1 | 6/2018 |
| WO | WO-2018175746 A1 | 9/2018 |
| WO | WO-2022086986 A1 | 4/2022 |
| WO | WO-2022241122 A1 | 11/2022 |
| WO | WO-2023086419 A1 | 5/2023 |
| WO | WO-2023114867 A2 | 6/2023 |
| WO | WO-2023150635 A1 | 8/2023 |
| WO | WO-2024097758 A1 | 5/2024 |
| WO | WO-2025016385 A1 | * 1/2025 ........... A61K 31/519 |
| WO | WO-2025019497 A2 | 1/2025 |

OTHER PUBLICATIONS

Borkin, D., "Pharmacologic inhibition of the Menin-MLL interaction blocks progression of MLL leukemia in vivo." Cancer cell 27.4 (2015): 589-602.*
Agarwal, S.K. et al. Menin Molecular Interactions: Insights into Normal Functions and Tumorigenesis. Hormone and Metabolic Research 37(6):369-374 (2005).
Ansel, Howard C. et al. Pharmaceutical Dosage Forms and Drug Delivery Systems, 7th Edition. Lippincott Williams & Wilkins (1999).
Bernstein, Joel. Crystal Structure Prediction and Polymorphism. ACA Transactions 39:14-23 (2004).
Braga, Dario. et al. Making Crystals from Crystals: a Green Route to Crystal Engineering and Polymorphism. Chemical Communications 29:3635-3645 (2005).
Co-pending U.S. Appl. No. 18/827,538, inventors Jing; Tao et al., filed Sep. 6, 2024.
Gennaro, Alfonso R. Remington: Practice of The Science and Pharmacy, 19th Edition. Mack Publishing Company (1995).
Hoover, John E. et al. Remington's Pharmaceutical Sciences. Mack Publishing Company 1-5 (1975).
International Conference on Harmonization of Technical Requirements for Registration of Pharmaceuticals for Human Use (ICH), "Impurities: Guidelines for Residual Solvents Q3C(R6)." 1-40 (Oct. 2016).
Jones, William et al. Pharmaceutical Cocrystals: An Emerging Approach to Physical Property Enhancement. MRS Bulletin 31:875-879 (2006).
Liberman, Herbert A, and Leon Lachman. Pharmaceutical Dosage Forms: Tablets. Marcel Decker 1-7 (1980).
PCT Application No. PCT/CN2024/092390, Inventors Bakale, Roger Paul et al., filed on May 10, 2024.
Price, Sarah L. The Computational Prediction of Pharmaceutical Crystal Structures and Polymorphism. Advanced Drug Delivery Reviews 56:301-319 (2004).
U.S. Appl. No. 63/600,575, inventors Burrows; Francis et al., filed Nov. 17, 2023.
U.S. Appl. No. 63/659,748, inventors Burrows; Francis et al., filed Jun. 13, 2024.
U.S. Appl. No. 63/680,376, inventor Leoni; Mollie, filed Aug. 7, 2024.
Yokoyama, Akihiko et al. The Menin Tumor Suppressor Protein is an Essential Oncogenic Cofactor for MLL-associated Leukemogenesis. Cell 123(2):207-218 (2005).
Fiskus, Warren, et al. Activity of menin inhibitor ziftomenib (KO-539) as monotherapy or in combinations against AML cells with MLL1 rearrangement or mutant NPM1. Leukemia 36:2729-2733 (2022).

(Continued)

*Primary Examiner* — John S Kenyon
(74) *Attorney, Agent, or Firm* — WILSON SONSINI GOODRICH & ROSATI

(57) ABSTRACT

Described herein are crystalline forms of (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile or solvate thereof.

35 Claims, 12 Drawing Sheets

(56) References Cited

OTHER PUBLICATIONS

Lei, Hao, et al. Recent Progress of Small Molecule Menin-MLL Interaction Inhibitors as Therapeutic Agents for Acute Leukemia. J. Med. Chem. 64:15519-15533 (2021).
PCT/CN2024/105761 International Search Report and Written Opinion dated Oct. 23, 2024.
Khadka, Prakash. et al. Pharmaceutical particle technologies: An approach to improve drug solubility, dissolution and bioavailability. Asian Journal of Pharmaceutical Sciences 9(6):304-316 (2014).
Morissette, Sherry L. et al. High-throughput Crystallization: Polymorphs, Salts, Co-crystals and Solvates of Pharmaceutical Solids. Advanced Drug Delivery Reviews 56(3):275-300 (2004).
Rowe, Raymond C. et al. Handbook of Pharmaceutical Excipients: A Comprehensive Guide to Uses, Properties, and Safety, 5th Edition. Pharmaceutical Press (2006).
U.S. Appl. No. 18/827,538 Office Action dated Jan. 16, 2025.

\* cited by examiner

CRYSTALLINE FORMS OF A MENIN INHIBITOR

CROSS-REFERENCE

This patent application is a continuation of International Application No. PCT/US2024/038216, filed Jul. 16, 2024, which claims the benefit of the U.S. Provisional Application Ser. No. 63/514,089 filed Jul. 17, 2023, and U.S. Provisional Application Ser. No. 63/655,384 filed Jun. 3, 2024, each of which is incorporated by reference herein in its entirety.

BACKGROUND

The mixed-lineage leukemia (MLL) protein is a histone methyltransferase critical for the epigenetic regulation of gene transcription. Many acute leukemias, including acute myeloblastic leukemia (AML), acute lymphoblastic leukemia (ALL) and mixed-lineage leukemia (MLL), are characterized by the presence of chimeric MLL fusion proteins that result from chromosomal translocations of the MLL gene located at chromosome 11, band q23 (11q23). Chimeric MLL fusion proteins retain approximately 1,400 amino acids of the N-terminus of MLL but are fused with one of approximately 80 partner proteins (e.g., AF4, AF9, ENL, AF10, ELL, AF6, AF1p, GAS7). MLL fusion proteins lack the original histone methyltransferase activity of the C-terminus of MLL and gain the ability to regulate transcription of numerous oncogenes, including HOX and MEIS1, resulting in increased cell proliferation and decreased cell differentiation, ultimately leading to leukemogenesis.

The menin protein, which is encoded by the Multiple Endocrine Neoplasia (MEN) gene, is a ubiquitously expressed nuclear protein that engages in interactions with DNA processing and repair proteins, chromatin modifying proteins and numerous transcription factors (Agarwal et al., Horm. Metab. Res. 2005, 37(6), 369-374). The association of menin with the N-terminus of MLL fusion proteins is necessary for the observed oncogenic activity of MLL fusion proteins. This association has been shown to constitutively up-regulate the expression of HOX and MEIS1 oncogenes and impairs proliferation and differentiation of hematopoietic cells leading to leukemia development. As menin has been shown to function as a general oncogenic cofactor in MLL-related leukemias, the interaction between menin and MLL fusion proteins and MLL represents a potential chemotherapeutic target.

SUMMARY OF THE INVENTION

In one aspect, described herein is a crystalline form of (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof.

In one embodiment of the crystalline form of (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile, the crystalline form of (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof is Form 1, having at least one of the following properties:
(a) an X-ray powder diffraction (XRPD) pattern substantially similar to the one set forth in FIG. 1;
(b) an XRPD pattern with at least three characteristic peaks selected from 4.1° 2-Theta, 5.4° 2-Theta, 6.6° 2-Theta, 8.2° 2-Theta, 9.5° 2-Theta, 12.3° 2-Theta, 13.1° 2-Theta, 13.9° 2-Theta, 15.9° 2-Theta, 16.4° 2-Theta, 17.0° 2-Theta, 17.5° 2-Theta, 19.7° 2-Theta, and 22.6° 2-Theta;
(c) a differential scanning calorimetry (DSC) thermogram substantially similar to the one set forth in FIG. 2;
(d) a DSC thermogram with an endotherm having an onset at about 136° C. and/or a peak at about 149° C.;
(e) a thermogravimetric analysis (TGA) curve substantially similar to the one set forth in FIG. 3; or
(f) combinations thereof.

In another embodiment of the crystalline form of (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile, the crystalline form of (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof is Form 2, having at least one of the following properties:
(a) an X-ray powder diffraction (XRPD) pattern substantially similar to the one set forth in FIG. 4;
(b) an XRPD pattern with at least three characteristic peaks selected from 3.8° 2-Theta, 5.6° 2-Theta, 6.4° 2-Theta, 7.1° 2-Theta, 8.8° 2-Theta, 9.9° 2-Theta, 11.9° 2-Theta, and 14.8° 2-Theta; or
(c) a combination thereof.

In another embodiment of the crystalline form of (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile, the crystalline form of (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof is Form 3, having at least one of the following properties:
(a) an X-ray powder diffraction (XRPD) pattern substantially similar to the one set forth in FIG. 5;
(b) an XRPD pattern with at least three characteristic peaks selected from 7.9° 2-Theta, 9.5° 2-Theta, 11.0° 2-Theta, 15.7° 2-Theta, 16.5° 2-Theta, 18.0° 2-Theta, 19.0° 2-Theta, and 21.9° 2-Theta;
(c) a differential scanning calorimetry (DSC) thermogram substantially similar to the one set forth in FIG. 6A;
(d) a DSC thermogram with an endotherm having an onset at about 117° C. and/or a peak at about 135° C.;
(e) a thermogravimetric analysis (TGA) curve substantially similar to the one set forth in FIG. 6B; or
(f) combinations thereof.

In another embodiment of the crystalline form of (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile, the crystalline form of (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof is Form 4, having at least one of the following properties:
(a) an X-ray powder diffraction (XRPD) pattern substantially similar to the one set forth in FIG. 7;
(b) an XRPD pattern with at least three characteristic peaks selected from 8.1° 2-Theta, 9.4° 2-Theta, 10.8°

2-Theta, 13.5° 2-Theta, 15.7° 2-Theta, 16.3° 2-Theta, 17.5° 2-Theta, 18.3° 2-Theta, 18.7° 2-Theta, 20.1° 2-Theta, 21.6° 2-Theta, 21.8° 2-Theta, 25.2° 2-Theta, and 25.7° 2-Theta;

(c) a differential scanning calorimetry (DSC) thermogram substantially similar to the one set forth in FIG. 8;

(d) a DSC thermogram with a first endotherm having an onset at about 127° C. and/or a peak at about 138° C., and optionally a second endotherm having an onset at about 45° C. and/or a peak at about 75° C.; or (e) combinations thereof.

In another embodiment of the crystalline form of (S)-4-methyl-5-((4-((2-(methylamino)-6-(2,2,2-trifluoroethyl) thieno[2,3-d]pyrimidin-4-yl)amino)piperidin-1-yl)methyl)-1-(2-(4-(methylsulfonyl)piperazin-1-yl)propyl)-1H-indole-2-carbonitrile, the crystalline form of (S)-4-methyl-5-((4-((2-(methylamino)-6-(2,2,2-trifluoroethyl)thieno[2,3-d] pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof is Form 5, having at least one of the following properties:

(a) an X-ray powder diffraction (XRPD) pattern substantially similar to the one set forth in FIG. 9;

(b) an XRPD pattern with at least three characteristic peaks selected from 7.9° 2-Theta, 8.5° 2-Theta, 9.6° 2-Theta, 11.1° 2-Theta, 15.8° 2-Theta, 16.9° 2-Theta, 18.4° 2-Theta, 19.1° 2-Theta, 22.1° 2-Theta, 25.5° 2-Theta, and 27.4° 2-Theta;

(c) a differential scanning calorimetry (DSC) thermogram substantially similar to the one set forth in FIG. 10;

(d) a DSC thermogram with an endotherm having an onset at about 122° C. and/or a peak at about 132° C.; or (e) a dynamic vapor sorption (DVS) curve substantially similar to the one set forth in FIG. 11; or (f) combinations thereof.

In another aspect, described herein is a pharmaceutical composition comprising a crystalline form of (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile or solvate thereof, and a pharmaceutically acceptable excipient.

In another aspect, described herein is a method for treating a disease or condition in a subject, comprising administering to the subject a therapeutically effective amount of a crystalline form of (S)-4-methyl-5-((4-((2-(methylamino)-6-(2,2,2-trifluoroethyl)thieno[2,3-d]pyrimidin-4-yl)amino) piperidin-1-yl)methyl)-1-(2-(4-(methylsulfonyl)piperazin-1-yl)propyl)-1H-indole-2-carbonitrile or solvate thereof described herein, wherein the disease or condition comprises a leukemia, acute myelogenous leukemia (AML), acute lymphoblastic leukemia (ALL), hematologic malignancy, myelodysplastic syndrome, myelodysplastic/myeloproliferative neoplasm, solid tumor cancer, prostate cancer, breast cancer, liver cancer, brain tumor, or diabetes.

In some embodiments is a method inhibiting an interaction of menin with one or more of MLL1, MLL2, an MLL fusion protein, and an MLL Partial Tandem Duplication, comprising contacting menin with an effective amount of a crystalline form of (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile or solvate thereof described herein.

INCORPORATION BY REFERENCE

All publications, patents, and patent applications mentioned in this specification are herein incorporated by reference to the extent applicable and relevant and to the same extent as if each individual publication, patent, or patent application was specifically and individually indicated to be incorporated by reference.

Figure 1:
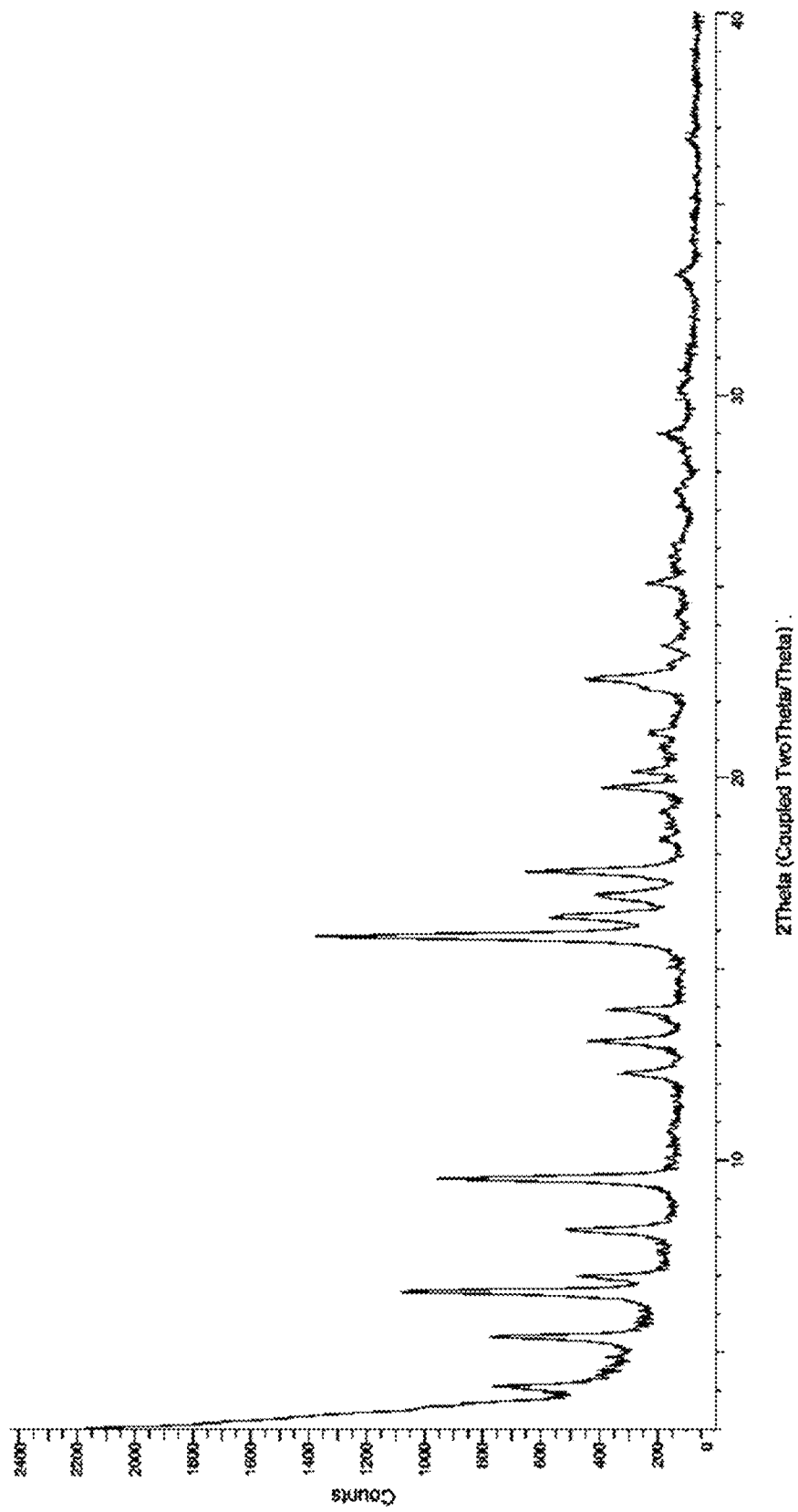
FIG. 1. Illustrates an XRPD pattern of crystalline (S)-4-methyl-5-((4-((2-(methylamino)-6-(2,2,2-trifluoroethyl) thieno[2,3-d]pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof, Form 1.

1-(2-(4-(methylsulfonyl)piperazin-1-yl)propyl)-1H-indole-2-carbonitrile (Compound 1) or solvate thereof, Form 5.

DETAILED DESCRIPTION OF THE INVENTION

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. The term "about" when referring to a number or a numerical range means that the number or numerical range referred to is an approximation within experimental variability (or within statistical experimental error), and thus the number or numerical range may vary between 1% and 15% of the stated number or numerical range.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety.

The term "acceptable" or "pharmaceutically acceptable" with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder, or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The terms "co-administration" or the like, as used herein, are meant to encompass administration of the selected therapeutic agents to a single patient and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of Compound 1, age, weight, general condition of the subject, the condition being treated, the severity of the condition being treated, and the judgment of the prescribing physician. By way of example only, therapeutically effective amounts may be determined by a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder, or condition. An "enhancing-effective amount," as used herein, refers to an amount adequate to enhance the effect of a therapeutic agent in the treatment of a disease, disorder, or condition. When used in a patient, amounts effective for this use will depend on the severity and course of the disease, disorder, or condition, previous therapy, the patient's health status and response to the drugs, and the judgment of the treating physician.

The term "prophylactically effective amount," as used herein, refers to that amount of a composition applied to a patient which will relieve to some extent one or more of the symptoms of a disease, condition or disorder being treated. In such prophylactic applications, such amounts may depend on the patient's state of health, weight, and the like. As an example, one can determine such prophylactically effective amounts by a dose escalation clinical trial.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "treat," "treating," or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating," or "treatment," include, but are not limited to, prophylactic and/or therapeutic treatments.

Compound 1

In one embodiment is (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof. "Compound 1" or "(S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile" refers to the free base compound with the following structure:

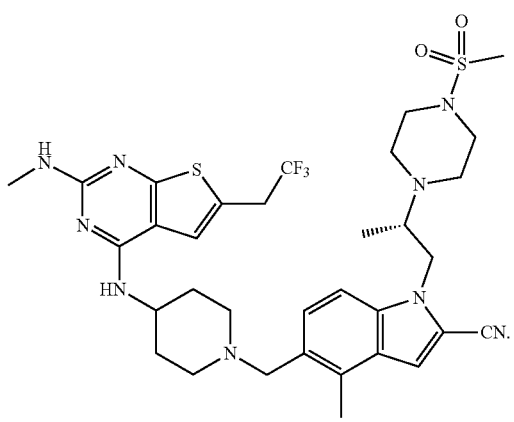

Compound 1 is a menin inhibitor and inhibits the menin-MLL interaction.

In some embodiments, described herein are crystalline forms of Compound 1 or solvates thereof. Solvates contain either stoichiometric or non-stoichiometric amounts of a solvent, and are formed during the process of product formation or isolation with pharmaceutically acceptable solvents such as water, ethanol (EtOH), methanol (MeOH), tert-butyl methyl ether (MTBE), diisopropyl ether, ethyl acetate (EtOAc), isopropyl acetate, isopropyl alcohol (IPA), methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile (ACN), and the like. In some embodiments, solvates are formed using, but not limited to, Class 3 solvent(s). In some embodiments, solvates are formed using, but not limited to, Class 2 solvent(s). Categories of solvents are defined in, for example, the International Conference on Harmonization of Technical Requirements for Registration of Pharmaceuticals for Human Use (ICH), "Impurities: Guidelines for Residual Solvents Q3C(R6)," (October 2016). Hydrates are formed when the solvent is water, or alcoholates are formed when the solvent is an alcohol, such as EtOH or IPA.

In other embodiments, Compound 1 or solvate thereof is prepared in various forms, including but not limited to, an amorphous phase and crystalline forms.

While not intending to be bound by any particular theory, certain solid forms are characterized by physical properties, e.g., stability, solubility, and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein.

Crystalline Forms

The identification and selection of a solid form of a pharmaceutical compound are complex, given that a change in solid form may affect a variety of physical and chemical properties, which may provide benefits or drawbacks in processing (e.g., flowability, bulk density), formulation, stability, bioavailability, storage, and handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability.

Whether crystalline or amorphous, solid forms of a pharmaceutical compound include single-component and multiple-component solids. Single-component solids consist essentially of the pharmaceutical compound or active ingredient in the absence of other compounds. Variety among single-component crystalline materials may potentially arise from the phenomenon of polymorphism, wherein multiple three-dimensional arrangements exist for a particular pharmaceutical compound.

Notably, it is not possible to predict apriori if crystalline forms of a compound even exist, let alone the physicochemical and biological properties of any one or more of such materials, or how to successfully prepare them (see, e.g., Braga and Grepioni, *Chem. Commun.* 2005, 29, 3635-3645 ("with respect to crystal engineering, if instructions are not very precise and/or if other external factors affect the process, the result can be unpredictable"); Jones et al., *MRS Bull.* 2006, 31, 875-879 ("At present it is not generally possible to computationally predict the number of observable polymorphs of even the simplest molecules"); Price, *Adv. Drug Deliv. Rev.* 2004, 56(3), 301-319; and Bernstein, *ACA Transactions* 2004, 39, 14-23 ("a great deal still needs to be learned and done before one can state with any degree of confidence the ability to predict a crystal structure, much less polymorphic forms")).

The variety of possible solid forms creates potential diversity in physical and chemical properties for a given pharmaceutical compound. The discovery and selection of solid forms are of great importance in the development of an effective, stable, and marketable pharmaceutical product.

Crystalline Compound 1, Form 1

Figure 2:
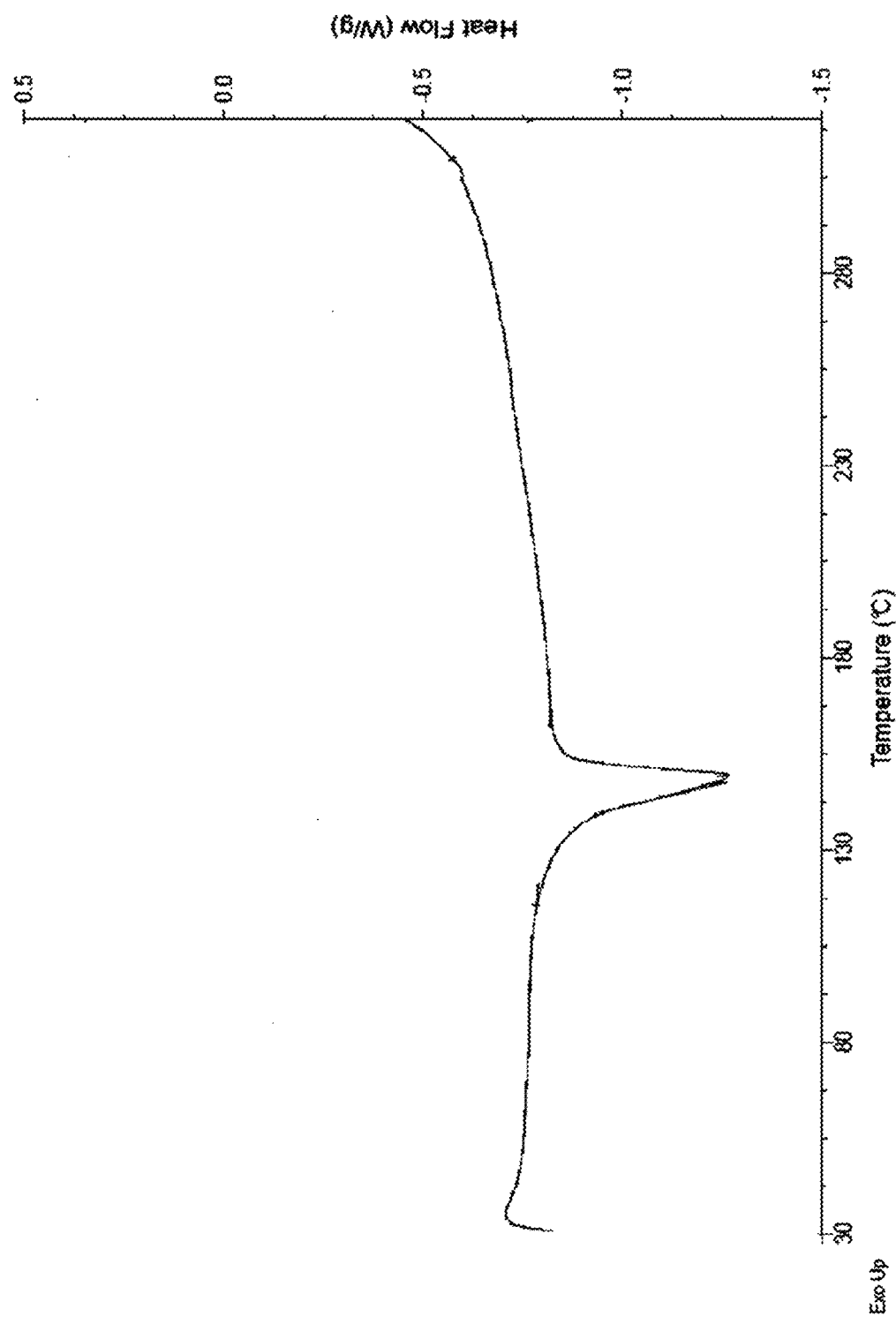
FIG. 2. Illustrates a DSC thermogram of crystalline (S)-4-methyl-5-((4-((2-(methylamino)-6-(2,2,2-trifluoroethyl)thieno[2,3-d]pyrimidin-4-yl)amino)piperidin-1-yl) methyl)-1-(2-(4-(methylsulfonyl)piperazin-1-yl)propyl)-1H-indole-2-carbonitrile (Compound 1) or solvate thereof, Form 1.
Figure 3:
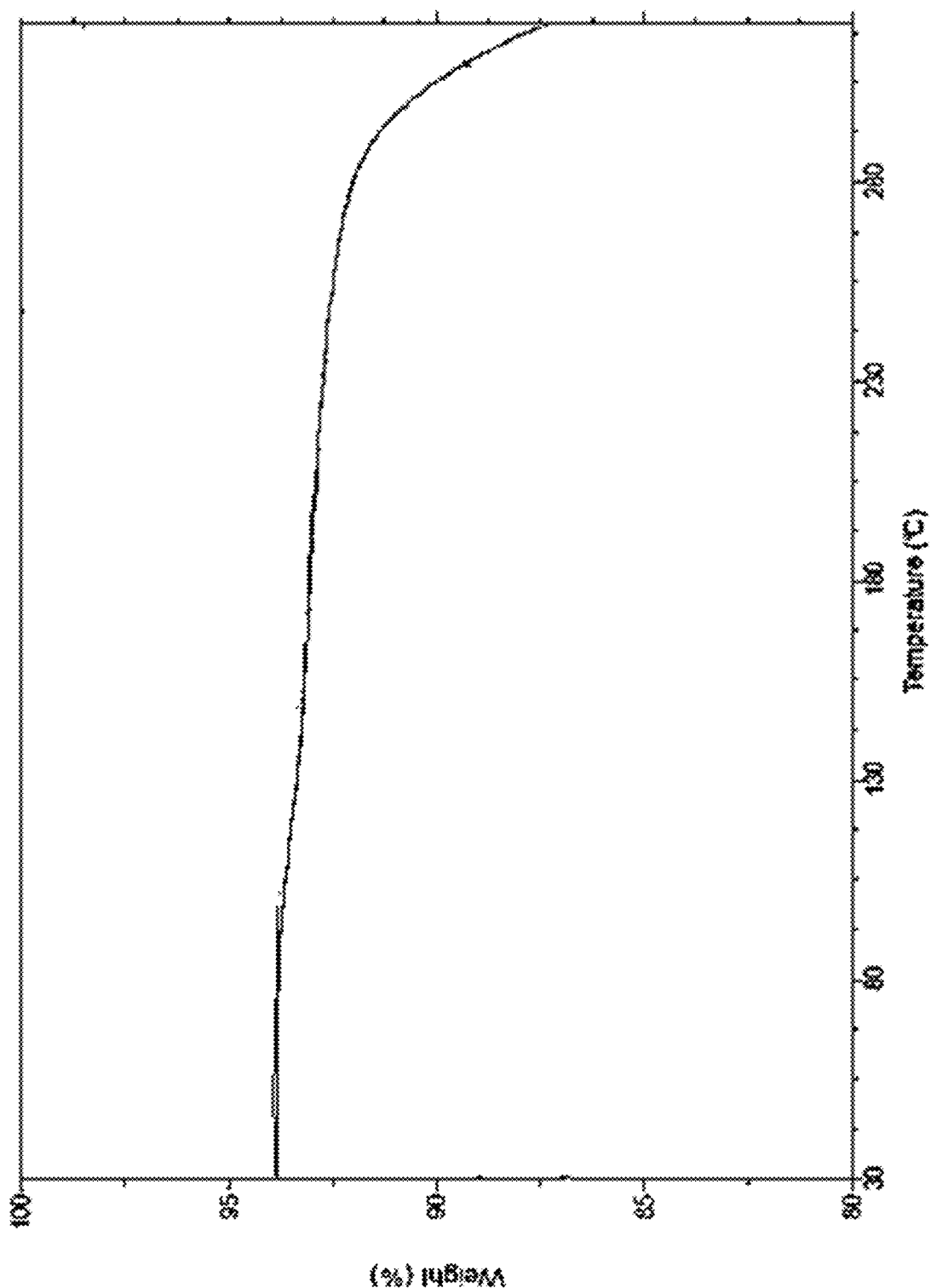
FIG. 3. Illustrates a TGA curve of crystalline (S)-4-methyl-5-((4-((2-(methylamino)-6-(2,2,2-trifluoroethyl) thieno[2,3-d]pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof, Form 1.

In some embodiments, the crystalline form of Compound 1 or solvate thereof is Form 1, characterized as having at least one of the following properties:
  (a) an XRPD pattern substantially similar to the one set forth in FIG. 1;
  (b) an XRPD pattern with at least three characteristic peaks selected from 4.1° 2-Theta, 5.4° 2-Theta, 6.6° 2-Theta, 8.2° 2-Theta, 9.5° 2-Theta, 12.3° 2-Theta, 13.1° 2-Theta, 13.9° 2-Theta, 15.9° 2-Theta, 16.4° 2-Theta, 17.0° 2-Theta, 17.5° 2-Theta, 19.7° 2-Theta, and 22.6° 2-Theta;
(c) a differential scanning calorimetry (DSC) thermogram substantially similar to the one set forth in FIG. 2;
(d) a DSC thermogram with an endotherm having an onset at about 136° C. and/or a peak at about 149° C.;
(e) a TGA curve substantially similar to the one set forth in FIG. 3; or
(f) combinations thereof.

In some embodiments, crystalline Compound 1, Form 1, is characterized as having at least two of the properties selected from (a) to (e). In some embodiments, crystalline Compound 1, Form 1, is characterized as having at least three of the properties selected from (a) to (e). In some embodiments, crystalline Compound 1, Form 1, is characterized as having at least four of the properties selected from (a) to (e). In some embodiments, crystalline Compound 1, Form 1, is characterized as having properties (a) to (e).

In some embodiments, crystalline Compound 1, Form 1, has an XRPD pattern substantially similar to the one set forth in FIG. 1. In some embodiments, crystalline Compound 1, Form 1, has an XRPD pattern with at least four characteristic peaks selected from 4.1° 2-Theta, 5.4° 2-Theta, 6.6° 2-Theta, 8.2° 2-Theta, 9.5° 2-Theta, 12.3° 2-Theta, 13.1° 2-Theta, 13.9° 2-Theta, 15.9° 2-Theta, 16.4° 2-Theta, 17.0° 2-Theta, 17.5° 2-Theta, 19.7° 2-Theta, and 22.6° 2-Theta. In some embodiments, crystalline Compound 1, Form 1, has an XRPD pattern with at least five characteristic peaks selected from 4.1° 2-Theta, 5.4° 2-Theta, 6.6° 2-Theta, 8.2° 2-Theta, 9.5° 2-Theta, 12.3° 2-Theta, 13.1° 2-Theta, 13.9° 2-Theta, 15.9° 2-Theta, 16.4° 2-Theta, 17.0° 2-Theta, 17.5° 2-Theta, 19.7° 2-Theta, and 22.6° 2-Theta. In some embodiments, crystalline Compound 1, Form 1, has an XRPD pattern with at least six characteristic peaks selected from 4.1° 2-Theta, 5.4° 2-Theta, 6.6° 2-Theta, 8.2° 2-Theta, 9.5° 2-Theta, 12.3° 2-Theta, 13.1° 2-Theta, 13.9° 2-Theta, 15.9° 2-Theta, 16.4° 2-Theta, 17.0° 2-Theta, 17.5° 2-Theta, 19.7° 2-Theta, and 22.6° 2-Theta. In some embodiments, crystalline Compound 1, Form 1, has an XRPD pattern with at least seven characteristic peaks selected from 4.1° 2-Theta, 5.4° 2-Theta, 6.6° 2-Theta, 8.2° 2-Theta, 9.5° 2-Theta, 12.3° 2-Theta, 13.1° 2-Theta, 13.9° 2-Theta, 15.9° 2-Theta, 16.4° 2-Theta, 17.0° 2-Theta, 17.5° 2-Theta, 19.7° 2-Theta, and 22.6° 2-Theta. In some embodiments, crystalline Compound 1, Form 1, has an XRPD pattern with at least eight, or at least nine, or at least 10, or at least 11, or at least 12, characteristic peaks selected from 4.1° 2-Theta, 5.4° 2-Theta, 6.6° 2-Theta, 8.2° 2-Theta, 9.5° 2-Theta, 12.3° 2-Theta, 13.1° 2-Theta, 13.9° 2-Theta, 15.9° 2-Theta, 16.4° 2-Theta, 17.0° 2-Theta, 17.5° 2-Theta, 19.7° 2-Theta, and 22.6° 2-Theta. In some embodiments, crystalline Compound 1, Form 1, has an XRPD pattern with characteristic peaks at 5.4° 2-Theta, 6.6° 2-Theta, 8.2° 2-Theta, 9.5° 2-Theta, 15.9° 2-Theta, 16.4° 2-Theta, 17.5° 2-Theta, and 22.6° 2-Theta. In some embodiments, crystalline Compound 1, Form 1, has an XRPD pattern with characteristic peaks at 4.1° 2-Theta, 5.4° 2-Theta, 6.6° 2-Theta, 8.2° 2-Theta, 9.5° 2-Theta, 12.3° 2-Theta, 13.1° 2-Theta, 13.9° 2-Theta, 15.9° 2-Theta, 16.4° 2-Theta, 17.0° 2-Theta, 17.5° 2-Theta, 19.7° 2-Theta, and 22.6° 2-Theta. In some embodiments, crystalline Compound 1, Form 1, has a DSC thermogram substantially similar to the one set forth in FIG. 2. In some embodiments, crystalline Compound 1, Form 1, has a DSC thermogram with an endotherm having an onset at about 136° C. In some embodiments, crystalline Compound 1, Form 1, has a DSC thermogram with an endotherm having a peak at about 149° C. In some embodiments, crystalline Compound 1, Form 1, has a TGA curve substantially similar to the one set forth in FIG. 3. In some embodiments, crystalline Compound 1, Form 1, has a TGA curve that exhibits a weight loss of about 0.60% over the range of about 29° C. to about 150° C. In some embodiments, crystalline Compound 1, Form 1, is an anhydrate. In some embodiments, crystalline Compound 1, Form 1, is obtained from a mixture of MEK and n-heptane. In some embodiments, crystalline Compound 1, Form 1, is obtained from toluene. In some embodiments, crystalline Compound 1, Form 1, is obtained from MTBE.

Crystalline Compound 1, Form 2

In some embodiments, the crystalline form of Compound 1 or solvate thereof is Form 2, characterized as having at least one of the following properties:
(a) an XRPD pattern substantially similar to the one set forth in FIG. 4;
(b) an XRPD pattern with at least three characteristic peaks selected from 3.8° 2-Theta, 5.6° 2-Theta, 6.4° 2-Theta, 7.1° 2-Theta, 8.8° 2-Theta, 9.9° 2-Theta, 11.9° 2-Theta, and 14.8° 2-Theta; or
(c) a combination thereof.

In some embodiments, crystalline Compound 1, Form 2, is characterized as having both of the properties (a) and (b).

Figure 4:
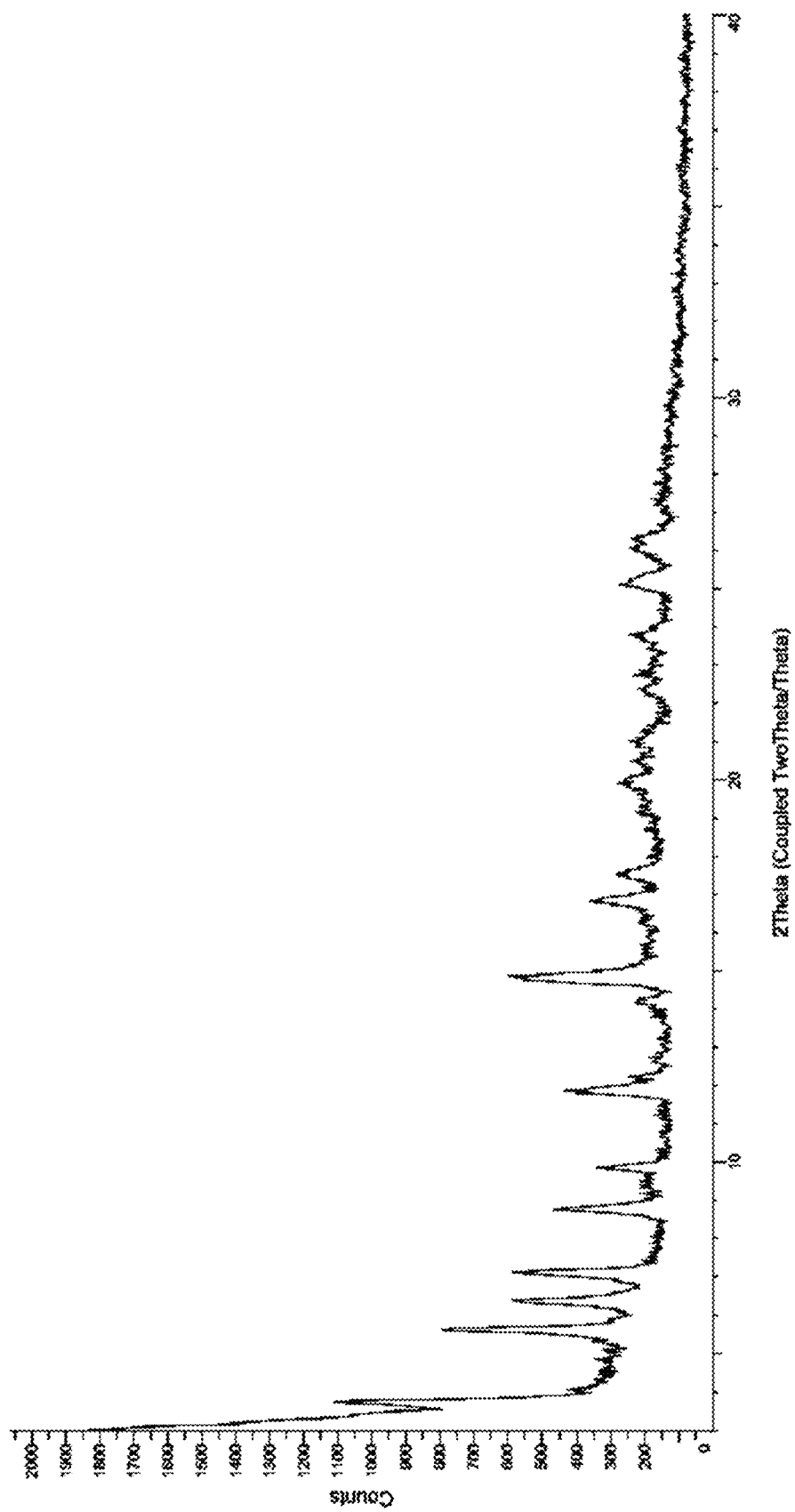
FIG. 4. Illustrates an XRPD pattern of crystalline (S)-4-methyl-5-((4-((2-(methylamino)-6-(2,2,2-trifluoroethyl) thieno[2,3-d]pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof, Form 2.

In some embodiments, crystalline Compound 1, Form 2, has an XRPD pattern substantially similar to the one set forth in FIG. 4. In some embodiments, crystalline Compound 1, Form 2, has an XRPD pattern with at least four characteristic peaks selected from 3.8° 2-Theta, 5.6° 2-Theta, 6.4° 2-Theta, 7.1° 2-Theta, 8.8° 2-Theta, 9.9° 2-Theta, 11.9° 2-Theta, and 14.8° 2-Theta. In some embodiments, crystalline Compound 1, Form 2, has an XRPD pattern with at least five characteristic peaks selected from 3.8° 2-Theta, 5.6° 2-Theta, 6.4° 2-Theta, 7.1° 2-Theta, 8.8° 2-Theta, 9.9° 2-Theta, 11.9° 2-Theta, and 14.8° 2-Theta. In some embodiments, crystalline Compound 1, Form 2, has an XRPD pattern with at least six, or at least seven, characteristic peaks selected from 3.8° 2-Theta, 5.6° 2-Theta, 6.4° 2-Theta, 7.1° 2-Theta, 8.8° 2-Theta, 9.9° 2-Theta, 11.9° 2-Theta, and 14.8° 2-Theta. In some embodiments, crystalline Compound 1, Form 2, has an XRPD pattern with peaks at 5.6° 2-Theta, 6.4° 2-Theta, 7.1° 2-Theta, 8.8° 2-Theta, 11.9° 2-Theta, and 14.8° 2-Theta. In some embodiments, crystalline Compound 1, Form 2, has an XRPD pattern with peaks at 3.8° 2-Theta, 5.6° 2-Theta, 6.4° 2-Theta, 7.1° 2-Theta, 8.8° 2-Theta, 9.9° 2-Theta, 11.9° 2-Theta, and 14.8° 2-Theta. In some embodiments, crystalline Compound 1, Form 2, is obtained from ACN. In some embodiments, crystalline Compound 1, Form 2, is an acetonitrile solvate.

Crystalline Compound 1, Form 3

In some embodiments, the crystalline form of Compound 1 or solvate thereof is Form 3, characterized as having at least one of the following properties:
(a) an XRPD pattern substantially similar to the one set forth in FIG. 5;
(b) an XRPD pattern with at least three characteristic peaks selected from 7.9° 2-Theta, 9.5° 2-Theta, 11.0° 2-Theta, 15.7° 2-Theta, 16.5° 2-Theta, 18.0° 2-Theta, 19.0° 2-Theta, and 21.9° 2-Theta;
(c) a DSC thermogram substantially similar to the one set forth in FIG. 6A;
(d) a DSC thermogram with an endotherm having an onset at about 117° C. and/or a peak at about 135° C.;
(e) a TGA curve substantially similar to the one set forth in FIG. 6B; or
(f) combinations thereof.

In some embodiments, crystalline Compound 1, Form 3, is characterized as having at least two of the properties selected from (a) to (e). In some embodiments, crystalline Compound 1, Form 3, is characterized as having at least three of the properties selected from (a) to (e). In some embodiments, crystalline Compound 1, Form 3, is characterized as having at least four of the properties selected from (a) to (e). In some embodiments, crystalline Compound 1, Form 3, is characterized as having properties (a) to (e).

Figure 5:
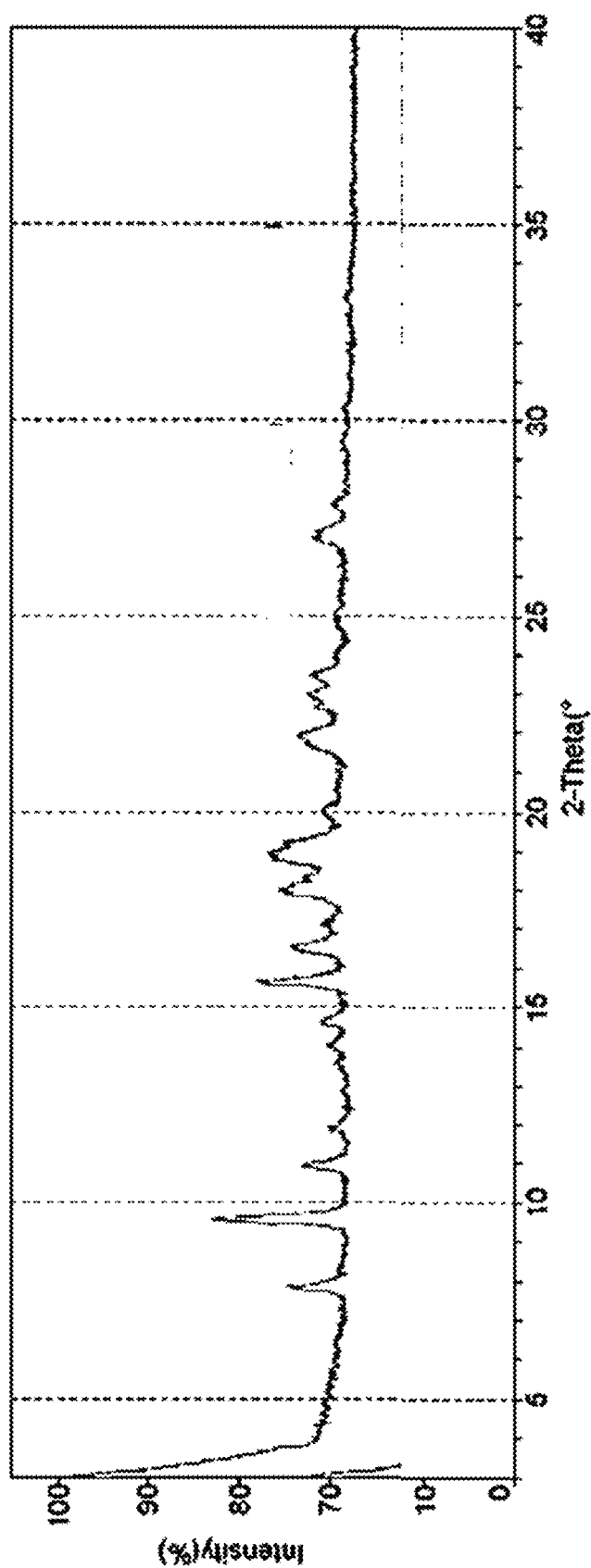
FIG. 5. Illustrates an XRPD pattern of crystalline (S)-4-methyl-5-((4-((2-(methylamino)-6-(2,2,2-trifluoroethyl) thieno[2,3-d]pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof, Form 3.
Figure 6A:
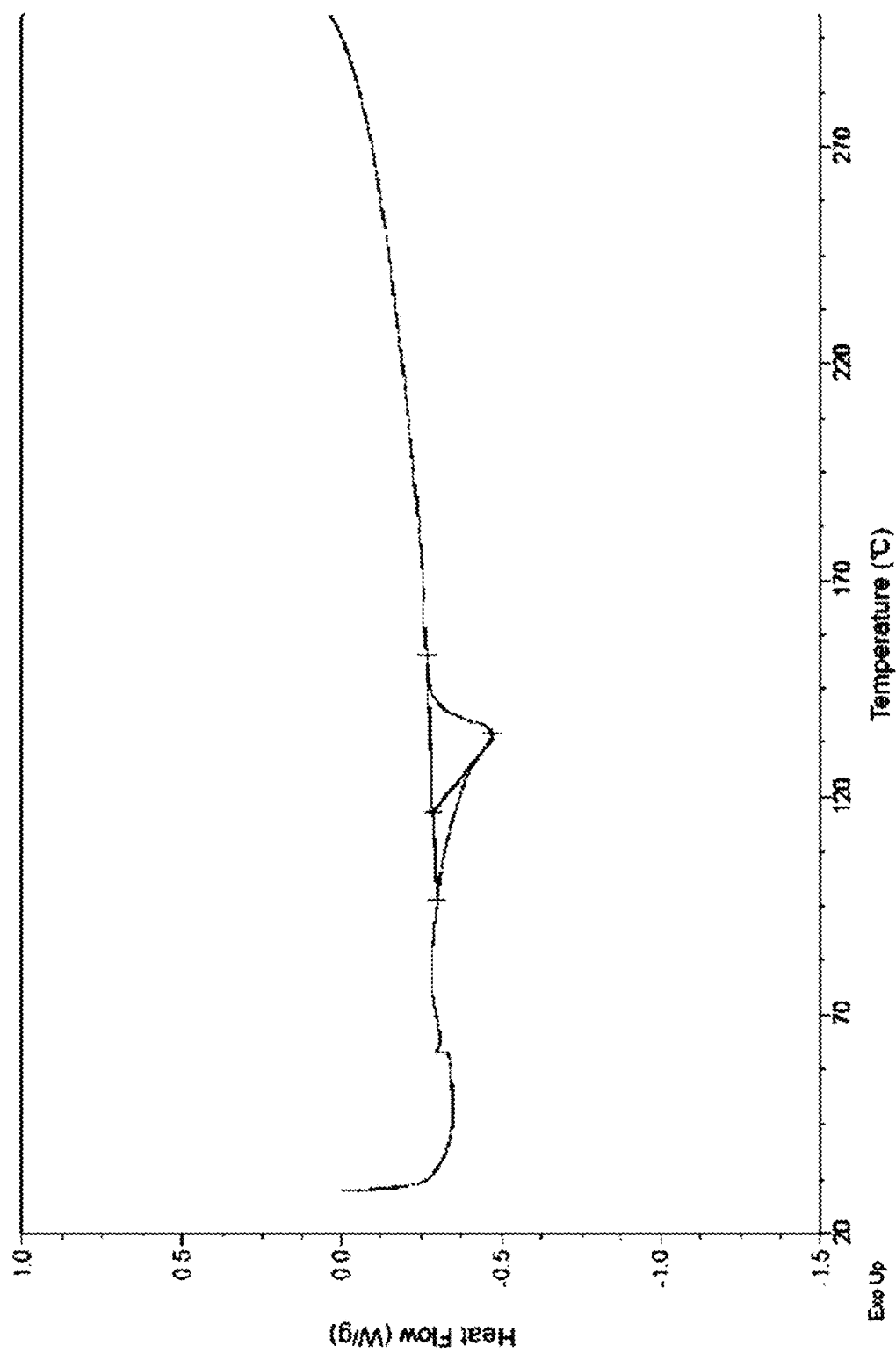
FIGS. 6A-6B. Illustrates a DSC thermogram (FIG. 6A) and a TGA curve (FIG. 6B; curve marked with asterisk) of crystalline (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof, Form 3.
Figure 6B:
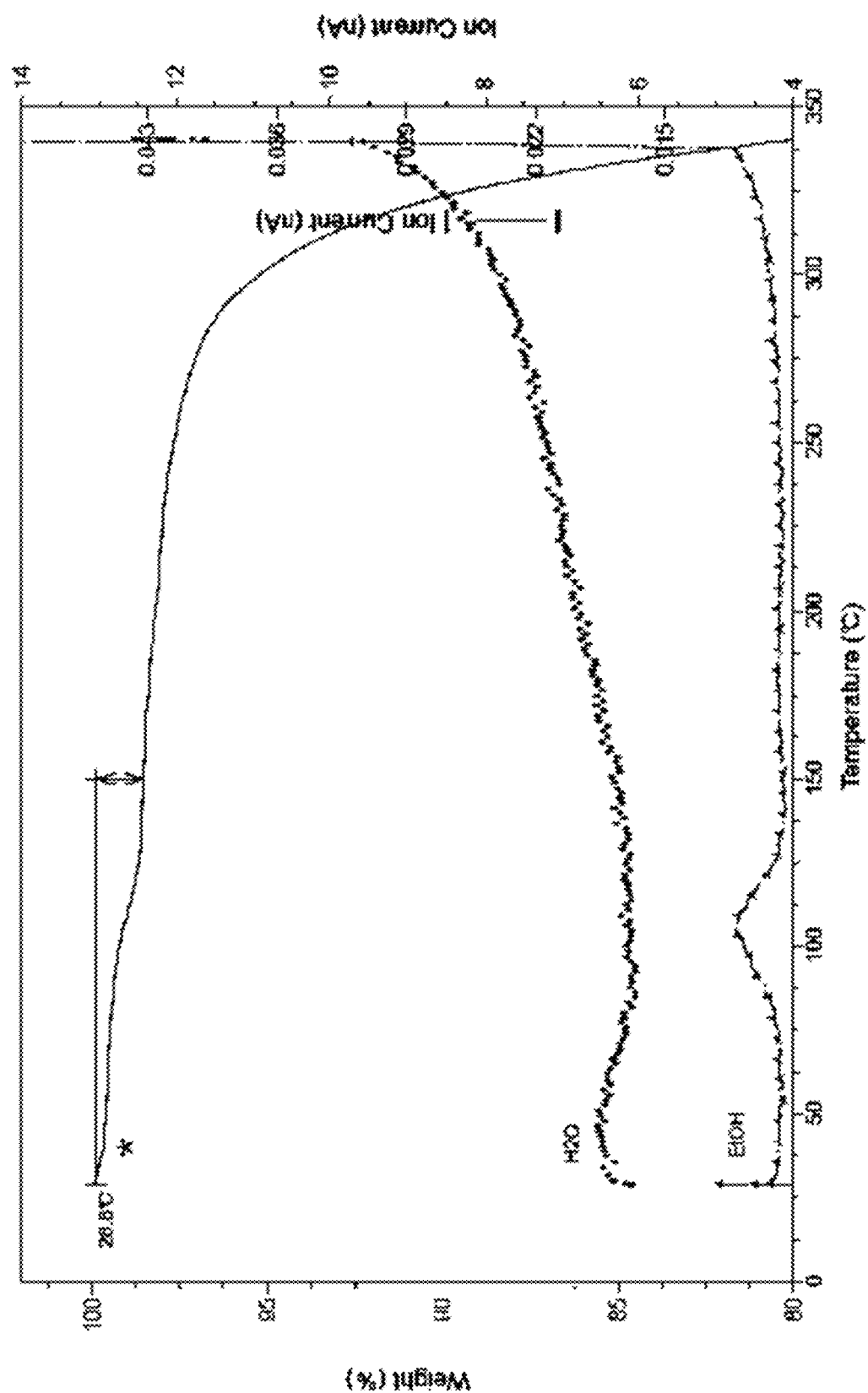

In some embodiments, crystalline Compound 1, Form 3, has an XRPD pattern substantially similar to the one set forth in FIG. 5. In some embodiments, crystalline Compound 1, Form 3, has an XRPD pattern with at least four characteristic peaks selected from 7.9° 2-Theta, 9.5° 2-Theta, 11.0° 2-Theta, 15.7° 2-Theta, 16.5° 2-Theta, 18.0° 2-Theta, 19.0° 2-Theta, and 21.9° 2-Theta. In some embodiments, crystalline Compound 1, Form 3, has an XRPD pattern with at least five characteristic peaks selected from 7.9° 2-Theta, 9.5° 2-Theta, 11.0° 2-Theta, 15.7° 2-Theta, 16.5° 2-Theta, 18.0° 2-Theta, 19.0° 2-Theta, and 21.9° 2-Theta. In some embodiments, crystalline Compound 1, Form 3, has an XRPD pattern with at least six characteristic peaks selected from 7.9° 2-Theta, 9.5° 2-Theta, 11.0° 2-Theta, 15.7° 2-Theta, 16.5° 2-Theta, 18.0° 2-Theta, 19.0° 2-Theta, and 21.9° 2-Theta. In some embodiments, crystalline Compound 1, Form 3, has an XRPD pattern with at least seven characteristic peaks selected from 7.9° 2-Theta, 9.5° 2-Theta, 11.0° 2-Theta, 15.7° 2-Theta, 16.5° 2-Theta, 18.0° 2-Theta, 19.0° 2-Theta, and 21.9° 2-Theta. In some embodiments, crystalline Compound 1, Form 3, has an XRPD pattern with characteristic peaks at 7.9° 2-Theta, 9.5° 2-Theta, 11.0° 2-Theta, 15.7° 2-Theta, 16.5° 2-Theta, 18.0° 2-Theta, 19.0° 2-Theta, and 21.9° 2-Theta. In some embodiments, crystalline Compound 1, Form 3, has a DSC thermogram substantially similar to the one set forth in FIG. 6A. In some embodiments, crystalline Compound 1, Form 3, has a DSC thermogram with an endotherm having an onset at about 117° C. In some embodiments, crystalline Compound 1, Form 3, has a DSC thermogram with an endotherm having a peak at about 135° C. In some embodiments, crystalline Compound 1, Form 3, has a TGA curve substantially similar to the one set forth in FIG. 6B. In some embodiments, crystalline Compound 1, Form 3, has a TGA curve that exhibits a weight loss of about 1.33% over the range of about 29° C. to about 150° C. In some embodiments, crystalline Compound 1, Form 3, is obtained from EtOH. In some embodiments, crystalline Compound 1, Form 3, is an EtOH solvate.

Crystalline Compound 1, Form 4

In some embodiments, the crystalline form of Compound 1 or solvate thereof is Form 4, characterized as having at least one of the following properties:
  (a) an XRPD pattern substantially similar to the one set forth in FIG. 7;
  (b) an XRPD pattern with at least three characteristic peaks selected from 8.1° 2-Theta, 9.4° 2-Theta, 10.8° 2-Theta, 13.5° 2-Theta, 15.7° 2-Theta, 16.3° 2-Theta, 17.5° 2-Theta, 18.3° 2-Theta, 18.7° 2-Theta, 20.1° 2-Theta, 21.6° 2-Theta, 21.8° 2-Theta, 25.2° 2-Theta, and 25.7° 2-Theta;
  (c) a DSC thermogram substantially similar to the one set forth in FIG. 8;
  (d) a DSC thermogram with a second endotherm having an onset at about 128° C. and/or a peak at about 138° C., and optionally a second endotherm having an onset at about 45° C. and/or a peak at about 75° C.; or
  (e) combinations thereof.

In some embodiments, crystalline Compound 1, Form 4, is characterized as having at least two of the properties selected from (a) to (d). In some embodiments, crystalline Compound 1, Form 4, is characterized as having at least three of the properties selected from (a) to (d). In some embodiments, crystalline Compound 1, Form 4, is characterized as having properties (a) to (d).

Figure 7:
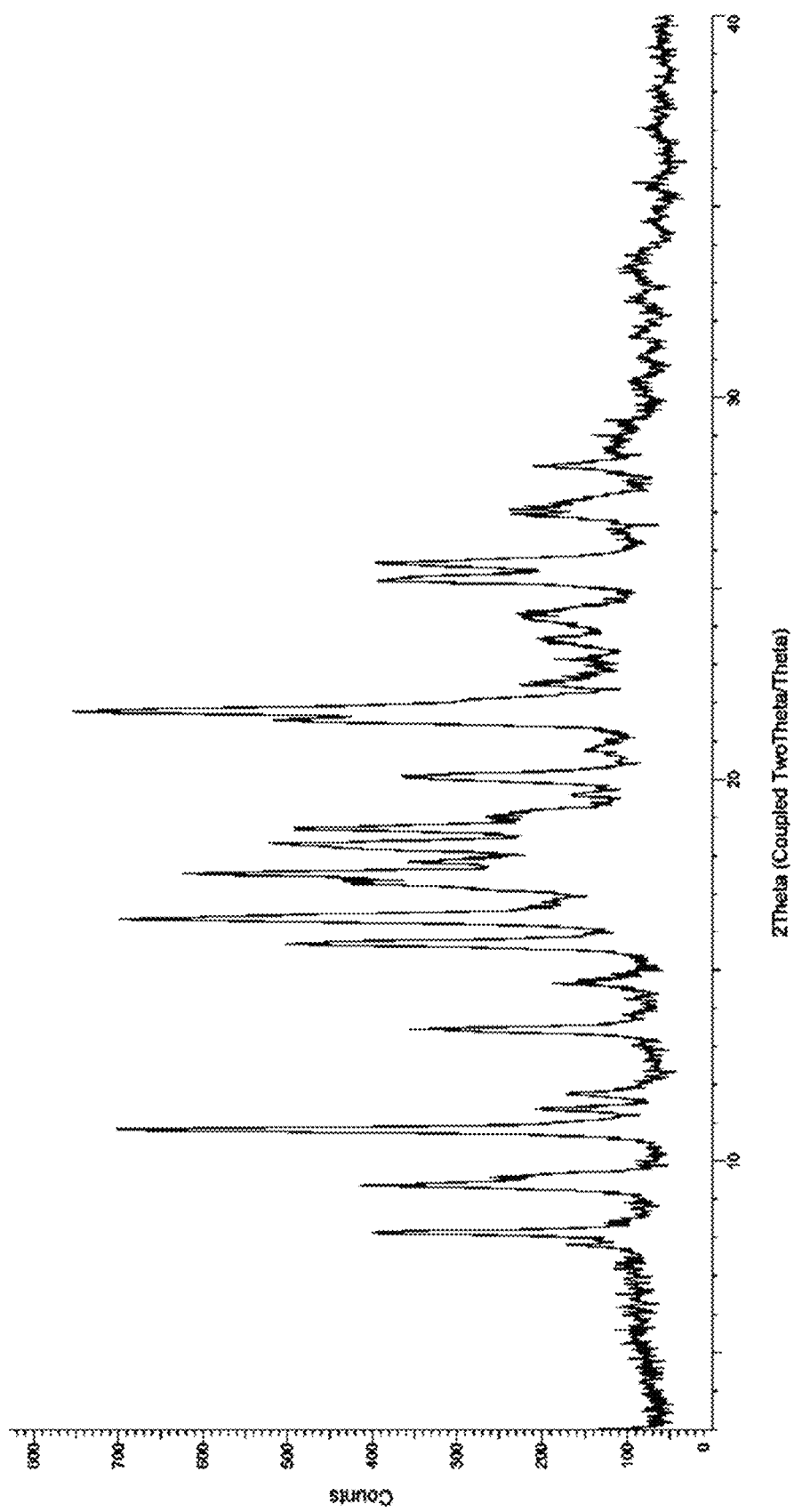
FIG. 7. Illustrates an XRPD pattern of crystalline (S)-4-methyl-5-((4-((2-(methylamino)-6-(2,2,2-trifluoroethyl) thieno[2,3-d]pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof, Form 4.
Figure 8:
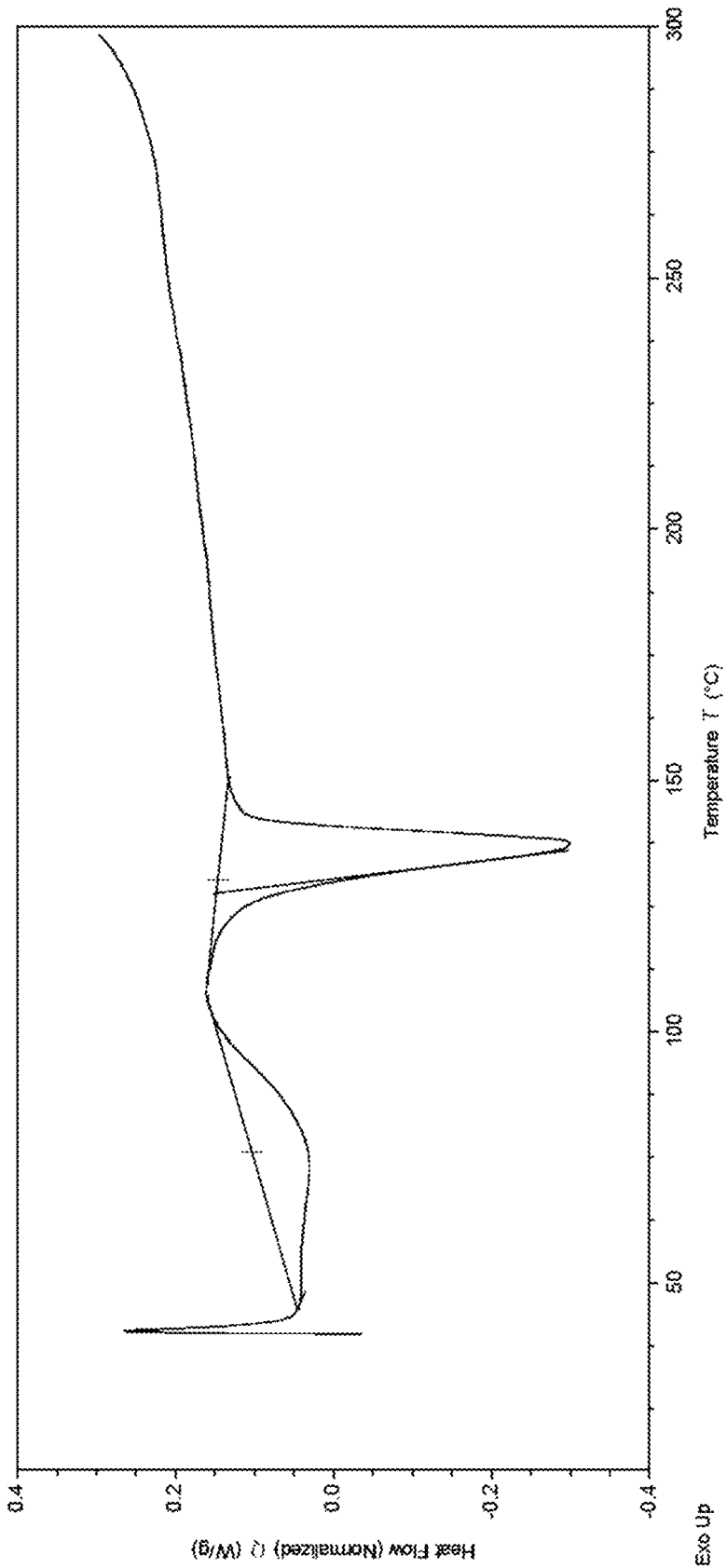
FIG. 8. Illustrates a DSC thermogram of crystalline (S)-4-methyl-5-((4-((2-(methylamino)-6-(2,2,2-trifluoroethyl)thieno[2,3-d]pyrimidin-4-yl)amino)piperidin-1-yl) methyl)-1-(2-(4-(methylsulfonyl)piperazin-1-yl)propyl)-1H-indole-2-carbonitrile (Compound 1) or solvate thereof, Form 4.

In some embodiments, crystalline Compound 1, Form 4, has an XRPD pattern substantially similar to the one set forth in FIG. 7. In some embodiments, crystalline Compound 1, Form 4, has an XRPD pattern with at least four characteristic peaks selected from 8.1° 2-Theta, 9.4° 2-Theta, 10.8° 2-Theta, 13.5° 2-Theta, 15.7° 2-Theta, 16.3° 2-Theta, 17.5° 2-Theta, 18.3° 2-Theta, 18.7° 2-Theta, 20.1° 2-Theta, 21.6° 2-Theta, 21.8° 2-Theta, 25.2° 2-Theta, and 25.7° 2-Theta. In some embodiments, crystalline Compound 1, Form 4, has an XRPD pattern with at least five characteristic peaks selected from 8.1° 2-Theta, 9.4° 2-Theta, 10.8° 2-Theta, 13.5° 2-Theta, 15.7° 2-Theta, 16.3° 2-Theta, 17.5° 2-Theta, 18.3° 2-Theta, 18.7° 2-Theta, 20.1° 2-Theta, 21.6° 2-Theta, 21.8° 2-Theta, 25.2° 2-Theta, and 25.7° 2-Theta. In some embodiments, crystalline Compound 1, Form 4, has an XRPD pattern with at least six characteristic peaks selected from 8.1° 2-Theta, 9.4° 2-Theta, 10.8° 2-Theta, 13.5° 2-Theta, 15.7° 2-Theta, 16.3° 2-Theta, 17.5° 2-Theta, 18.3° 2-Theta, 18.7° 2-Theta, 20.1° 2-Theta, 21.6° 2-Theta, 21.8° 2-Theta, 25.2° 2-Theta, and 25.7° 2-Theta. In some embodiments, crystalline Compound 1, Form 4, has an XRPD pattern with at least seven characteristic peaks selected from 8.1° 2-Theta, 9.4° 2-Theta, 10.8° 2-Theta, 13.5° 2-Theta, 15.7° 2-Theta, 16.3° 2-Theta, 17.5° 2-Theta, 18.3° 2-Theta, 18.7° 2-Theta, 20.1° 2-Theta, 21.6° 2-Theta, 21.8° 2-Theta, 25.2° 2-Theta, and 25.7° 2-Theta. In some embodiments, crystalline Compound 1, Form 4, has an XRPD pattern with at least eight, or at least nine, or at least 10, or at least 11, or at least 12, or at least 13 characteristic peaks selected from 8.1° 2-Theta, 9.4° 2-Theta, 10.8° 2-Theta, 13.5° 2-Theta, 15.7° 2-Theta, 16.3° 2-Theta, 17.5° 2-Theta, 18.3° 2-Theta, 18.7° 2-Theta, 20.1° 2-Theta, 21.6° 2-Theta, 21.8° 2-Theta, 25.2° 2-Theta, and 25.7° 2-Theta. In some embodiments, crystalline Compound 1, Form 4, has an XRPD pattern with characteristic peaks at 10.8° 2-Theta, 15.7° 2-Theta, 16.3° 2-Theta, 17.5° 2-Theta, 18.3° 2-Theta, 18.7° 2-Theta, 21.6° 2-Theta, and 21.8° 2-Theta. In some embodiments, crystalline Compound 1, Form 4, has an XRPD pattern with characteristic peaks at 8.1° 2-Theta, 9.4° 2-Theta, 10.8° 2-Theta, 13.5° 2-Theta, 15.7° 2-Theta, 16.3° 2-Theta, 17.5° 2-Theta, 18.3° 2-Theta, 18.7° 2-Theta, 20.1° 2-Theta, 21.6° 2-Theta, 21.8° 2-Theta, 25.2° 2-Theta, and 25.7° 2-Theta. In some embodiments, crystalline Compound 1, Form 4, has a DSC thermogram substantially similar to the one set forth in FIG. 8. In some embodiments, crystalline Compound 1, Form 4, has a DSC thermogram with a first endotherm having an onset at about 127° C. and/or a peak at about 138° C. and, optionally a second endotherm at about 45° C. and/or a peak at about 75° C. In some embodiments, crystalline Compound 1, Form 4, is obtained from EtOH, propanol, or IPA, or a mixture thereof. In some embodiments, crystalline Compound 1, Form 4, is obtained from EtOH. In some embodiments, crystalline Compound 1, Form 4, is obtained from propanol. In some embodiments, crystalline Compound 1, Form 4, is obtained from IPA. In some embodiments, crystalline Compound 1, Form 4, is obtained from a mixture of two or more of EtOH, propanol, and IPA. In some embodiments, crystalline Compound 1, Form 4, is a hydrate.

Crystalline Compound 1, Form 5

Figure 10:
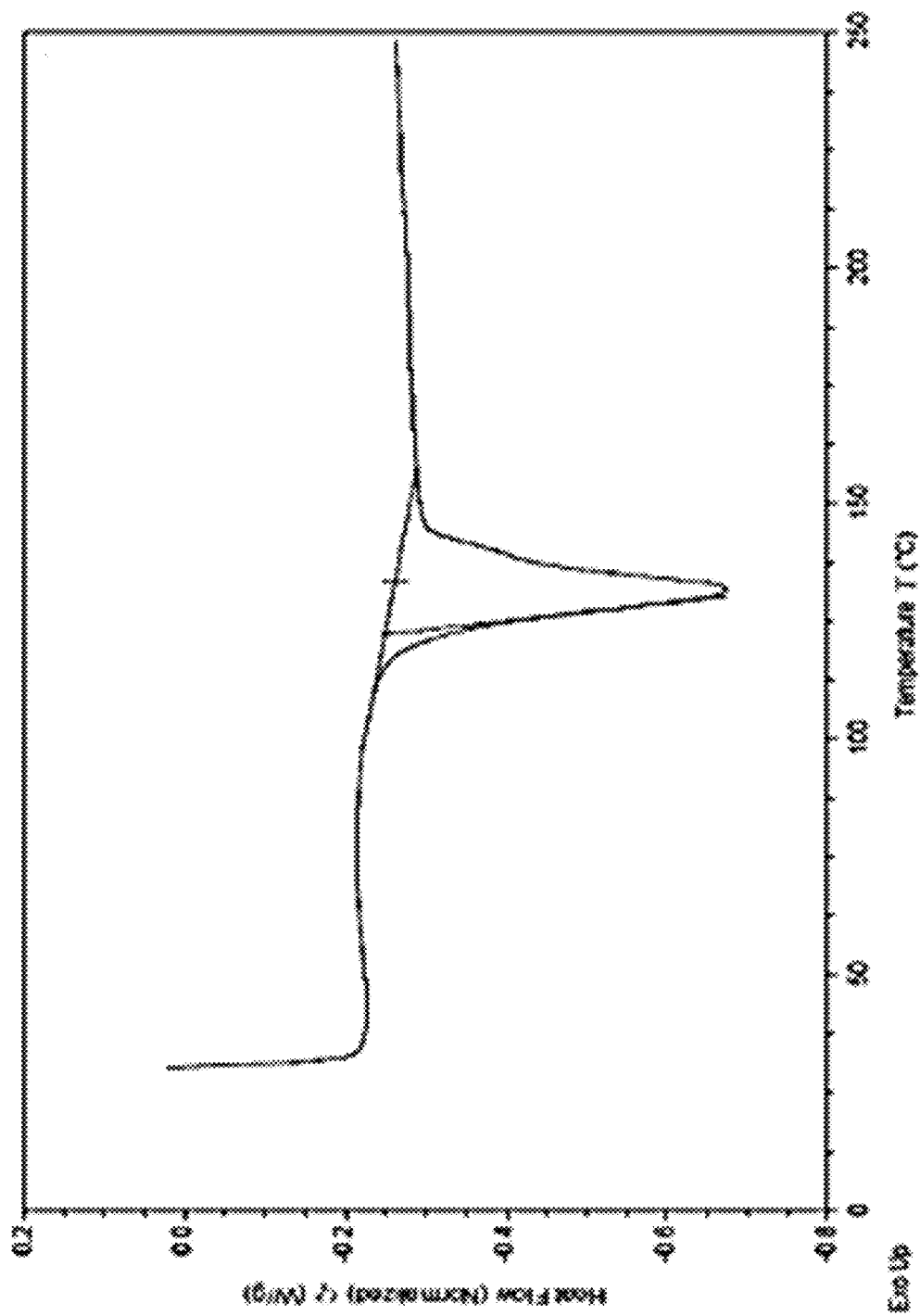
FIG. 10. Illustrates a DSC thermogram of crystalline (S)-4-methyl-5-((4-((2-(methylamino)-6-(2,2,2-trifluoroethyl)thieno[2,3-d]pyrimidin-4-yl)amino)piperidin-1-yl) methyl)-1-(2-(4-(methylsulfonyl)piperazin-1-yl)propyl)-1H-indole-2-carbonitrile (Compound 1) or solvate thereof, Form 5.
Figure 11:
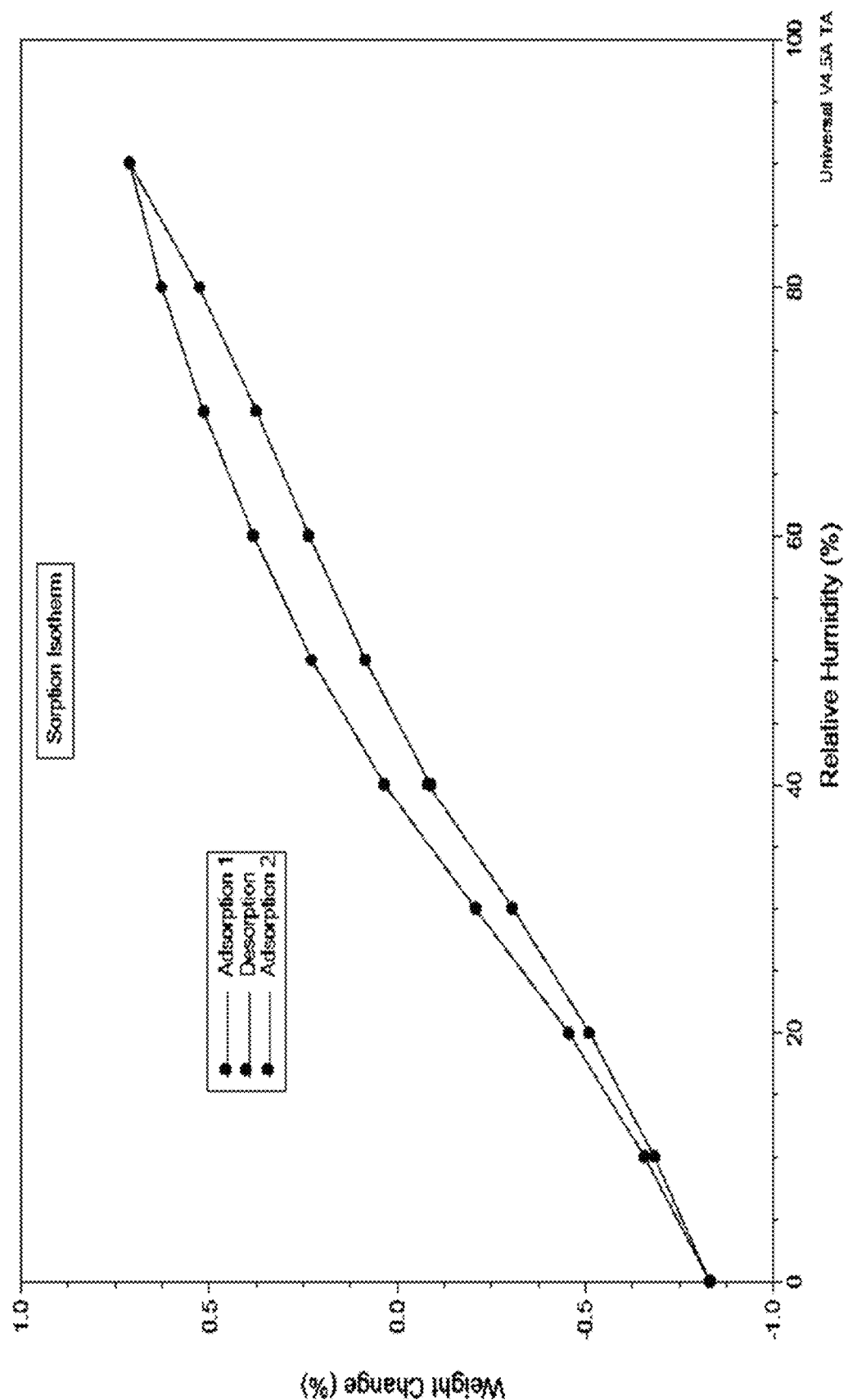
FIG. 11. Illustrates a DVS curve of crystalline (S)-4-methyl-5-((4-((2-(methylamino)-6-(2,2,2-trifluoroethyl) thieno[2,3-d]pyrimidin-4-yl)amino)piperidin-1-yl)methyl)-

In some embodiments, the crystalline form of Compound 1 is Form 5, characterized as having at least one of the following properties:
(a) an XRPD pattern substantially similar to the one set forth in FIG. 9;
(b) an XRPD pattern with at least three characteristic peaks selected from 7.9° 2-Theta, 8.5° 2-Theta, 9.6° 2-Theta, 11.1° 2-Theta, 15.8° 2-Theta, 16.9° 2-Theta, 18.4° 2-Theta, 19.1° 2-Theta, 22.1° 2-Theta, 25.5° 2-Theta, and 27.4° 2-Theta;
(c) a DSC thermogram substantially similar to the one set forth in FIG. 10;
(d) a DSC thermogram having an onset at about 122° C. and/or a peak at about 132° C.;
(e) a DVS curve substantially similar to the one set forth in FIG. 11; or
(f) combinations thereof.

In some embodiments, crystalline Compound 1, Form 5, is characterized as having at least two of the properties selected from (a) to (e). In some embodiments, crystalline Compound 1, Form 5, is characterized as having at least three of the properties selected from (a) to (e). In some embodiments, crystalline Compound 1, Form 5, is characterized as having at least four of the properties selected from (a) to (e). In some embodiments, crystalline Compound 1, Form 5, is characterized as having properties (a) to (e).

Figure 9:
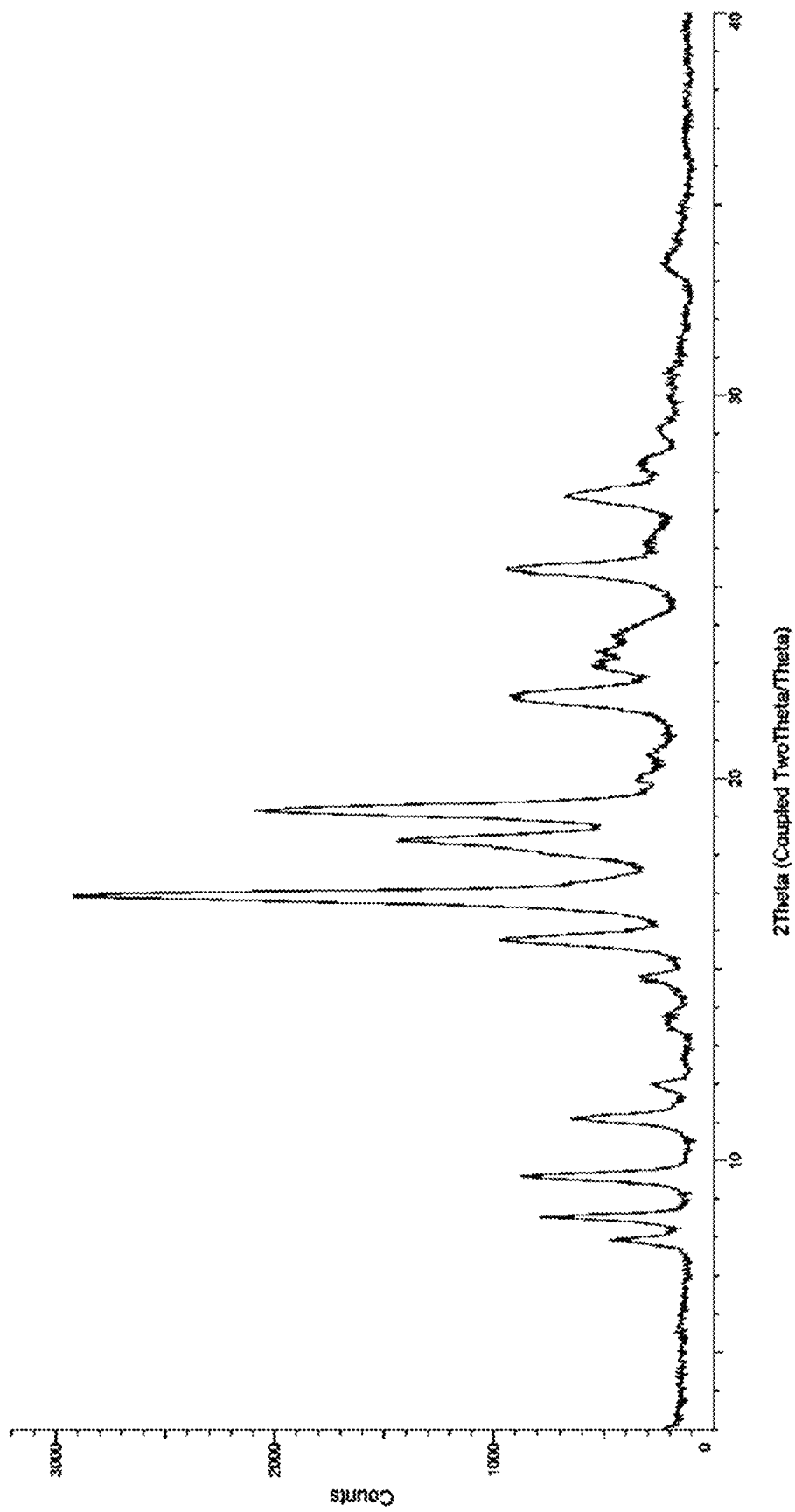
FIG. 9. Illustrates an XRPD pattern of crystalline (S)-4-methyl-5-((4-((2-(methylamino)-6-(2,2,2-trifluoroethyl) thieno[2,3-d]pyrimidin-4-yl)amino)piperidin-1-yl)methyl)-1-(2-(4-(methylsulfonyl)piperazin-1-yl)propyl)-1H-indole-2-carbonitrile (Compound 1) or solvate thereof, Form 5.

In some embodiments, crystalline Compound 1, Form 5, has an XRPD pattern substantially similar to the one set forth in FIG. 9. In some embodiments, crystalline Compound 1, Form 5, has an XRPD pattern with at least four characteristic peaks selected from 7.9° 2-Theta, 8.5° 2-Theta, 9.6° 2-Theta, 11.1° 2-Theta, 15.8° 2-Theta, 16.9° 2-Theta, 18.4° 2-Theta, 19.1° 2-Theta, 22.1° 2-Theta, 25.5° 2-Theta, and 27.4° 2-Theta. In some embodiments, crystalline Compound 1, Form 5, has an XRPD pattern with at least five characteristic peaks selected from 7.9° 2-Theta, 8.5° 2-Theta, 9.6° 2-Theta, 11.1° 2-Theta, 15.8° 2-Theta, 16.9° 2-Theta, 18.4° 2-Theta, 19.1° 2-Theta, 22.1° 2-Theta, 25.5° 2-Theta, and 27.4° 2-Theta. In some embodiments, crystalline Compound 1, Form 5, has an XRPD pattern with at least six characteristic peaks selected from 7.9° 2-Theta, 8.5° 2-Theta, 9.6° 2-Theta, 11.1° 2-Theta, 15.8° 2-Theta, 16.9° 2-Theta, 18.4° 2-Theta, 19.1° 2-Theta, 22.1° 2-Theta, 25.5° 2-Theta, and 27.4° 2-Theta. In some embodiments, crystalline Compound 1, Form 5, has an XRPD pattern with at least seven characteristic peaks selected from 7.9° 2-Theta, 8.5° 2-Theta, 9.6° 2-Theta, 11.1° 2-Theta, 15.8° 2-Theta, 16.9° 2-Theta, 18.4° 2-Theta, 19.1° 2-Theta, 22.1° 2-Theta, 25.5° 2-Theta, and 27.4° 2-Theta. In some embodiments, crystalline Compound 1, Form 5, has an XRPD pattern with at least eight, or at least nine, or at least 10 characteristic peaks selected from 7.9° 2-Theta, 8.5° 2-Theta, 9.6° 2-Theta, 11.1° 2-Theta, 15.8° 2-Theta, 16.9° 2-Theta, 18.4° 2-Theta, 19.1° 2-Theta, 22.1° 2-Theta, 25.5° 2-Theta, and 27.4° 2-Theta. In some embodiments, crystalline Compound 1, Form 5, has an XRPD pattern with characteristic peaks at 8.5° 2-Theta, 9.6° 2-Theta, 15.8° 2-Theta, 16.9° 2-Theta, 18.4° 2-Theta, 19.2° 2-Theta, 22.2° 2-Theta, and 25.5° 2-Theta. In some embodiments, crystalline Compound 1, Form 5, has an XRPD pattern with characteristic peaks at 7.9° 2-Theta, 8.5° 2-Theta, 9.6° 2-Theta, 11.1° 2-Theta, 15.8° 2-Theta, 16.9° 2-Theta, 18.4° 2-Theta, 19.1° 2-Theta, 22.1° 2-Theta, 25.5° 2-Theta, and 27.4° 2-Theta. In some embodiments, crystalline Compound 1, Form 5, has a DSC thermogram substantially similar to the one set forth in FIG. 10. In some embodiments, crystalline Compound 1, Form 5, has a DSC thermogram with an endotherm having an onset at about 122° C. In some embodiments, crystalline Compound 1, Form 5, has a DSC thermogram with an endotherm having a peak at about 132° C. In some embodiments, crystalline Compound 1, Form 5, has a DVS curve substantially similar to the one set forth in FIG. 11. In some embodiments, crystalline Compound 1, Form 5, is obtained from EtOH, optionally followed by drying. In some embodiments, crystalline Compound 1, Form 5, is an anhydrate. In some embodiments, crystalline Compound 1, Form 5, has residual EtOH content of less than 0.1%, or of about 0.05%, and residual water content as measured by KF analysis of about 0.5%.

Preparation of Crystalline Compound 1

In some embodiments, crystalline forms of Compound 1 or solvate thereof are prepared as outlined in the Examples. It is noted that solvents, temperatures and other reaction conditions presented herein may vary.

In another embodiment, crystalline Compound 1, Form 1, is substantially pure. In certain embodiments, the substantially pure crystalline Compound 1, Form 1, is substantially free of other solid forms, e.g., amorphous solid. In certain embodiments, the purity of the substantially pure crystalline Compound 1, Form 1, is no less than about 95%, no less than about 96%, no less than about 97%, no less than about 98%, no less than about 98.5%, no less than about 99%, no less than about 99.5%, or no less than about 99.8%.

In another embodiment, crystalline Compound 1, Form 2, is substantially pure. In certain embodiments, the substantially pure crystalline Compound 1, Form 2, is substantially free of other solid forms, e.g., amorphous solid. In certain embodiments, the purity of the substantially pure crystalline Compound 1, Form 2, is no less than about 95%, no less than about 96%, no less than about 97%, no less than about 98%, no less than about 98.5%, no less than about 99%, no less than about 99.5%, or no less than about 99.8%.

In another embodiment, crystalline Compound 1, Form 3, is substantially pure. In certain embodiments, the substantially pure crystalline Compound 1, Form 3, is substantially free of other solid forms, e.g., amorphous solid. In certain embodiments, the purity of the substantially pure crystalline Compound 1, Form 3, is no less than about 95%, no less than about 96%, no less than about 97%, no less than about 98%, no less than about 98.5%, no less than about 99%, no less than about 99.5%, or no less than about 99.8%.

In another embodiment, crystalline Compound 1, Form 4, is substantially pure. In certain embodiments, the substantially pure crystalline Compound 1, Form 4, is substantially free of other solid forms, e.g., amorphous solid. In certain embodiments, the purity of the substantially pure crystalline Compound 1, Form 4, is no less than about 95%, no less than about 96%, no less than about 97%, no less than about 98%, no less than about 98.5%, no less than about 99%, no less than about 99.5%, or no less than about 99.8%.

In another embodiment, crystalline Compound 1, Form 5, is substantially pure. In certain embodiments, the substantially pure crystalline Compound 1, Form 5, is substantially free of other solid forms, e.g., amorphous solid. In certain embodiments, the purity of the substantially pure crystalline Compound 1, Form 5, is no less than about 95%, no less than about 96%, no less than about 97%, no less than about 98%, no less than about 98.5%, no less than about 99%, no less than about 99.5%, or no less than about 99.8%.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. In some embodiments, solvents disclosed herein are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents Q3C(R6)," (October 2016).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: ACN, chlorobenzene, chloroform, cumene, cyclohexane, 1,2-dichloroethene, DCM, 1,2-dimethoxyethane, N,N-dimethylacetamide (DMA), N,N-dimethylformamide, 1,4-dioxane, 2-ethoxyethanol, ethylene glycol, formamide, hexane, MeOH, 2-methoxyethanol, methylbutyl ketone, methylcyclohexane, MIBK, N-methylpyrrolidone, nitromethane, pyridine, sulfolane, THF, tetralin, toluene, 1,1,2-trichloroethene and xylene.

Class 3 solvents, which possess low toxicity, include: acetic acid, acetone, anisole, 1-butanol, 2-butanol, butyl acetate, MTBE, dimethylsulfoxide (DMSO), EtOH, EtOAc, diethyl ether, ethyl formate, formic acid, heptane, isobutyl acetate, isopropyl acetate, methyl acetate, 3-methyl-1-butanol, MEK, 2-methyl-1-propanol, pentane, 1-pentanol, 1-propanol, IPA, propyl acetate, and triethylamine.

Residual solvents in active pharmaceutical ingredients (APIs) originate from the manufacture of APIs. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising a crystalline form of Compound 1 or solvate thereof comprise an organic solvent(s). In some embodiments, compositions comprising a crystalline form of Compound 1 or solvate thereof comprise a residual amount of an organic solvent(s). In some embodiments, compositions comprising a crystalline form of Compound 1 or solvate thereof comprise a residual amount of a Class 3 solvent. In some embodiments, the organic solvent is a Class 3 solvent, for example a Class 3 solvent listed above. In some embodiments, the Class 3 solvent is selected from the group consisting of acetone, EtOAc, isopropyl acetate, MTBE, heptane, IPA, and EtOH. In some embodiments, the organic solvent is a Class 2 solvent, for example a Class 2 solvent listed above. In some embodiments, the Class 2 solvent is ACN, THF, or toluene. In some embodiments, the Class 2 solvent is ACN. In some embodiments, the organic solvent is 2-butanone or 2-methyltetrahydrofuran (2-MeTHF).

Pharmaceutical Compositions/Formulations

In some embodiments is a pharmaceutical composition comprising crystalline Compound 1, and a pharmaceutically acceptable excipient. In some embodiments is a pharmaceutical composition comprising Compound 1, Form 2, Form 3, Form 4, or Form 5, and a pharmaceutically acceptable excipient. Pharmaceutical compositions comprising crystalline Compound 1, or Compound 1, Form 2, Form 3, Form 4, or Form 5, may be formulated in a conventional manner. Pharmaceutically acceptable excipients may include, for example, diluents, fillers, binders, disintegrants, glidants, lubricants, carriers, stabilizers, dispersing agents, suspending agents, surfactants, and thickening agents, as well as capsule shells or tablet coatings.

Methods

In some embodiments is a method of treating a disease or condition in a subject, wherein the disease or condition comprises a leukemia, acute myelogenous leukemia, acute lymphoblastic leukemia, hematologic malignancy, myelodysplastic syndrome, myelodysplastic/myeloproliferative neoplasm, solid tumor cancer, prostate cancer, breast cancer, liver cancer, brain tumor, or diabetes, comprising administering to the subject a crystalline form of Compound 1 or solvate thereof described herein, or a pharmaceutical composition comprising Compound 1 or solvate thereof, or comprising a crystalline form of Compound 1 or solvate thereof, such as a therapeutically effective amount of such compound or pharmaceutical composition as described herein. In some embodiments, the crystalline form of Compound 1 is Compound 1, Form 1, or Compound 1, Form 2, or Compound 1, Form 3, or Compound 1, Form 4, or Compound 1, Form 5. In practicing the methods of treatment or use provided herein, a therapeutically effective amount of Compound 1 or solvate thereof is administered, for example in a pharmaceutical composition, to a mammal having a disease, disorder, or condition to be treated. In some embodiments, the mammal is a human. A therapeutically effective amount can vary widely depending on the severity of the disease, the age and relative health of the subject, the potency of the compound used and other factors. In some embodiments is a method for treating a leukemia, optionally wherein the leukemia is AML or ALL, comprising administering to the subject in need thereof a therapeutically effective amount of a crystalline form of Compound 1 or solvent thereof described herein. In some embodiments, the AML is menin-dependent AML, KMT2A-rearranged AML, or NPM1-mutant AML. In some embodiments, the ALL is KTM2A-rearranged ALL.

EXAMPLES

I. Characterization of Polymorphs

Example 1: X-Ray Powder Diffraction (XRPD)

X-ray powder diffraction studies were performed using a Bruker D8 Advance with the following instrument parameters: X-Ray wavelength: Cu: K-Alpha (1=1.54179); X-Ray tube setting: Voltage: 40 kV; Current 40 mA Scan scope: 4° (2θ) to 40° (2θ); Sample rotation speed: 15 rpm; Scanning rate: 10 deg/min.

XRPD analysis of Form 1 of Compound 1 (FIG. 1) showed Form 1 to be crystalline with characteristic peaks at 4.1° 2-Theta, 5.4° 2-Theta, 6.6° 2-Theta, 8.2° 2-Theta, 9.5° 2-Theta, 12.3° 2-Theta, 13.1° 2-Theta, 13.9° 2-Theta, 15.9° 2-Theta, 16.4° 2-Theta, 17.0° 2-Theta, 17.5° 2-Theta, 19.7° 2-Theta, and 22.6° 2-Theta.

XRPD analysis of Form 2 of Compound 1 (FIG. 4) showed Form 2 to be crystalline with characteristic peaks at 3.8° 2-Theta, 5.6° 2-Theta, 6.4° 2-Theta, 7.1° 2-Theta, 8.8° 2-Theta, 9.9° 2-Theta, 11.9° 2-Theta, and 14.8° 2-Theta.

XRPD analysis of Form 3 of Compound 1 (FIG. 5) showed Form 3 to be crystalline with characteristic peaks at 7.9° 2-Theta, 9.5° 2-Theta, 11.0° 2-Theta, 15.7° 2-Theta, 16.5° 2-Theta, 18.0° 2-Theta, 19.0° 2-Theta, and 21.9° 2-Theta.

XRPD analysis of Form 4 of Compound 1 (FIG. 7) showed Form 4 to be crystalline with characteristic peaks at 8.1° 2-Theta, 9.4° 2-Theta, 10.8° 2-Theta, 13.5° 2-Theta, 15.7° 2-Theta, 16.3° 2-Theta, 17.5° 2-Theta, 18.3° 2-Theta, 18.7° 2-Theta, 20.1° 2-Theta, 21.6° 2-Theta, 21.8° 2-Theta, 25.2° 2-Theta, and 25.7° 2-Theta.

XRPD analysis of Form 5 of Compound 1 (FIG. 9) showed Form 5 to be crystalline with characteristic peaks at 7.9° 2-Theta, 8.5° 2-Theta, 9.6° 2-Theta, 11.1° 2-Theta, 15.8° 2-Theta, 16.9° 2-Theta, 18.4° 2-Theta, 19.1° 2-Theta, 22.1° 2-Theta, 25.5° 2-Theta, and 27.4° 2-Theta.

Example 2: Differential Scanning Calorimetry (DSC)

DSC studies were performed using a TA Discovery Q2000 or DSC250. The sample was weighed in crimped aluminum pan and the accurate amount was recorded. The sample was heated from room temperature or 30° C. to 250° C. or 300° C. at a heating rate of 10° C./min with nitrogen purge.

DSC analysis of Form 1 of Compound 1 (FIG. 2) showed an endotherm with onset at about 136° C. DSC analysis of Form 1 of Compound 1 (FIG. 2) showed an endotherm with a peak at about 149° C.

DSC analysis of Form 3 of Compound 1 (FIG. 6A) showed an endotherm with onset at about 117° C. and/or a peak at about 135° C.

DSC analysis of Form 4 of Compound 1 (FIG. 8) showed an endotherm having an onset at about 45° C. and a peak at about 75° C., and an endotherm having an onset at about 127° C. and a peak at about 138° C.

DSC analysis of Form 5 of Compound 1 (FIG. 10) showed a melting endotherm with onset at about 122° C. and a peak at about 132° C.

Example 3: Thermogravimetric Analysis/Dynamic Vapor Sorption

Thermogravimetric analysis of solid was performed using TA Q5000IR. The sample was placed in an open platinum pan and the amount was weighed automatically. The sample was heated from 30° C. to 300° C. at a heating rate of 10° C./min.

TGA of Form 1 of Compound 1 (FIG. 3) showed about 0.6% weight loss over the range of about 29° C. to about 150° C.

TGA of Form 3 of Compound 1 (FIG. 6B) showed about 1.33% weight loss over the range of about 29° C. to about 150° C.

Dynamic vapor sorption testing was performed at 25° C., with 10-15 mg of sample, under $N_2$ at a flow rate of 200 mL/min, and drying at 0% relative humidity for 120 min.

DVS of Form 5 of Compound 1 (FIG. 11) was obtained. Compound 1, Form 5, contained less than 0.1%, or about 0.05%, residual EtOH, and KF analysis showed residual water content of about 0.5%.

II. Polymorph Screen

Example 4: Solid Vapor Diffusion

Solid vapor diffusion experiments were performed using 14 different solvents. Approximate 10 mg of amorphous Compound 1 (free base) was weighed into a 4-mL vial, which was placed into a 40-mL vial with 3 mL of volatile solvent. The 40-mL vial was sealed with a cap and kept at ambient laboratory conditions for 1 day to allow solvent vapor to interact with sample. For clear solutions, slow evaporation was allowed at ambient laboratory conditions to induce crystallization. The obtained solids were tested by XRPD. Results are summarized in Table 1. Compound 1, Form 1, and Compound 1, Form 2, were generated via solid vapor diffusion in toluene and ACN, respectively.

TABLE 1

| Solvent | Solid Form |
| --- | --- |
| Water | Amorphous |
| DCM | Amorphous |
| EtOH | Quasi-amorphous |
| MeOH | Amorphous |
| ACN | Form 2 |
| THF | Amorphous |
| Toluene | Form 1 |
| Acetone | Amorphous |
| DMA | Gel |
| EtOAc | Quasi-amorphous |
| 1,4-Dioxane | Oil |
| IPA | Amorphous |
| DMSO | Amorphous |
| MTBE | Amorphous |

Example 5: Slurry at 25° C.

Slurry conversion experiments were conducted at 25° C. in different solvent systems. About 10-20 mg of amorphous Compound 1 was weighed into 0.5 mL of solvent in a 2-mL glass vial and then vortexed for about 2 min to mix well. After shaking at 25° C. for two days, clear solutions were obtained for all solvents except for MeOH/$H_2O$ (3:1, v/v), IPA, MTBE, and toluene. The 12 solvent systems with clear solutions were stored at 4° C. refrigerator to induce crystallization. No precipitates were observed. Slow evaporation gave solids under ambient laboratory conditions and the solids were tested by XRPD. Results are summarized in Table 2. Compound 1, Form 1, was generated as shown below. The EtOH experiment provided a crystalline form, Form 3, as indicated by XRPD, with a DSC with a broad endotherm over the range of about 95° C. to 150° C., with an onset of about 117° C. and a peak at about 135° C., and a TGA showing a weight loss of about 1.3% over the range of about 29° C. to 150° C. (DSC and TGA not shown). Compound 1, Form 3, was characterized as an EtOH solvate. Form 3 was heated at 90° C. and then vacuum-dried, Form 5 was obtained. Form 5 was characterized as an anhydrate. Solution crystallization of Compound 1 from EtOH and drying of the resulting solid also produced Form 5 following drying.

TABLE 2

| Solvent | Weight (mg) | Solid Form |
| --- | --- | --- |
| MeOH/$H_2O$ (3:1) | 10 | Amorphous |
| EtOH | 10 | Form 3 |
| IPA | 10 | Gel |
| 1-Butanol | 10 | Gel |
| ACN | 10 | Quasi-amorphous |
| Acetone/heptane(1:1) | 10 | Amorphous |
| MEK | 20 | Gel |
| MIBK | 20 | Gel |
| EtOAc | 20 | Gel |

TABLE 2-continued

| Solvent | Weight (mg) | Solid Form |
|---|---|---|
| Isopropyl acetate | 20 | Gel |
| MTBE | 10 | Form 1 |
| THF | 20 | Gel |
| 2-MeTHF | 20 | Gel |
| Toluene | 10 | Form 1 |
| DCM | 10 | Amorphous |
| 1,4-Dioxane | 10 | Gel |

Example 6: Slow Evaporation

Amorphous Compound 1 samples (10 mg each) were weighed into clean glass vials, and selected solvents were added to dissolve samples. If a sample did not dissolve completely, the solid was removed by filtration and the filtrate was collected into another vial. Each vial was covered with Parafilm with some pinholes. The solvent was allowed to evaporate at ambient temperature. Any solid precipitates from the resulting suspensions were collected and analyzed by XRPD. Results are summarized in Table 3 and show that no crystalline material was obtained.

TABLE 3

| Solvent | Solid Form |
|---|---|
| MeOH | Amorphous |
| EtOH | Amorphous |
| ACN | Amorphous |
| Acetone | Amorphous |
| MEK | Amorphous |
| MIBK | Amorphous |
| EtOAc | Amorphous |
| Isopropyl acetate | Amorphous |
| THF | Amorphous |
| 2-MeTHF | Amorphous |
| DCM | Amorphous |
| 1,4-Dioxane | Gel |

Example 7: Solution Vapor Diffusion

Solution vapor diffusion experiments were conducted with 14 solvent conditions under ambient laboratory conditions. Approximately 10 mg of amorphous Compound 1 was dissolved in 0.5 mL of a Solvent (Table 4) to obtain a clear solution in a 4-mL vial. Each vial was then placed into a 40-mL glass vial with 4 mL of a volatile Anti-solvent (Table 4). The 40-mL vial was sealed with a cap and kept at ambient conditions to allow sufficient time for organic vapor to interact with the solution. For clear solutions, slow evaporation was allowed to induce crystallization at ambient laboratory conditions. Any precipitates were isolated for XRPD analysis. As summarized in Table 4, no crystalline solids were formed.

TABLE 4

| Solvent | Anti-solvent | Solid Form |
|---|---|---|
| MeOH | 1-Butanol | Gel |
| MeOH | Water | Amorphous |
| EtOH | IPA | Gel |
| EtOH | Toluene | Gel |
| Acetone | Water | Quasi-amorphous |
| Acetone | Heptane | Amorphous |
| ACN | MTBE | Oil |
| ACN | Water | Amorphous |

TABLE 4-continued

| Solvent | Anti-solvent | Solid Form |
|---|---|---|
| DCM | IPA | Amorphous |
| DCM | Heptane | Amorphous |
| EtOAc | MTBE | Gel |
| EtOAc | Toluene | Gel |
| DMSO | 1-Butanol | N/A |
| DMSO | Water | Amorphous |

Example 8: Preparation of Compound 1, Form 4

A sample of Compound 1, Form 3, was exposed to 35° C. to 40° C. and 65 to 75% relative humidity conditions to provide Compound 1, Form 4 (1.2% water by Karl Fischer analysis).

Example 9: Preparation of Compound 1, Form 5

A solution of Compound 1 (free base) in 11.5V EtOH was heated at 55° C., then cooled to 30° C., seeded with 1% wt Form 3, stirred at 30° C. for 15 h, cooled to −5° C. over 7 h, stirred at −5° C. for 19 h. The resulting solid was filtered and washed with 2V EtOH and was dried at 50° C. under vacuum to yield Compound 1, Form 5 (0.05% residual EtOH, 0.5% water by Karl Fischer analysis).

Example 10: Compound 1, Form 1, and Compound 1, Form 5, Interconversion Study

Saturated solutions of Compound 1, Form 1, in EtOH, MTBE, and isopropyl acetate at 50° C. were prepared. About 6 mg of Compound 1, Form 1, and Compound 1, Form 5, were weighed into each saturated solutions, and the resulting suspensions were slurried for 2 days at corresponding temperature. The resulting solids were sampled for XRPD analysis. As shown in Table 5, Compound 1, Form 1, is a thermodynamically stable crystalline form.

TABLE 5

| Sample | Anti-solvent volume (µL) | Temp | XRPD after 1 day |
|---|---|---|---|
| Compound 1, Form 1, and Compound 1, Form 5 | EtOH | 25° C. | Form 1 and Form 3 |
|  |  | 50° C. | Amorphous |
| Compound 1, Form 1, and Compound 1, Form 5 | MTBE | 25° C. | Form 1 |
|  |  | 50° C. | Form 1 |
| Compound 1, Form 1, and Compound 1, Form 5 | iPrOAc | 25° C. | Form 1 |
|  |  | 50° C. | Form 1 |

Example 11: Compound 1, Forms 1, 4, and 5, Interconversion Studies

Treatment of 1:1 mixtures of Form 1 and Form 4 in IPA, IPA/water, MTBE, or CPME at 5 or 50° C. for up to 20 h, or acetone/water at 25° C. for up to 24 h, yielded predominantly or completely Form 1, and in water, at 5 or 50° C. for up to 20 h, yielded a mixture of Forms 1 and 4.

Treatment of 1:1 mixtures of Form 1 and Form 5 in IPAc, IPA, n-PrOH, or toluene, at 25° C., for up to 24 h, yielded Form 1.

Treatment of 1:1:1 mixtures of Forms 1, 4, and 5 in mixtures of water and IPA at 25° C. for up to 24 h yielded Form 1.

Treatment of Form 5 at 40° C., 75% relative humidity for 6 days provided mainly Form 4.

Treatment of Form 4 at 50° C. under vacuum and inert atmosphere for 5 days provided mainly Form 4.

II. Biological Data

Example 12: Fluorescence Polarization Assay

Fluorescence polarization (FP) competition experiments were performed to determine the effectiveness with which Compound 1 inhibits the menin-MLL interaction, reported as an $IC_{50}$ value. A fluorescein-labeled peptide containing the high affinity menin binding motif found in MLL was produced according to Yokoyama et al. (Cell, 2005, 123(2): 207-218). Binding of the labeled peptide (1.7 kDa) to the much larger menin (~67 kDa) is accompanied by a significant change in the rotational correlation time of the fluorophore, resulting in a substantial increase in the fluorescence polarization and fluorescence anisotropy (excitation at 500 nm, emission at 525 nm). The effectiveness with which Compound 1 inhibits the menin-MLL interaction was measured in an FP competition experiment, wherein a decrease in fluorescence anisotropy correlates with inhibition of the interaction and was used as a read-out for $IC_{50}$ determination: Compound 1, $IC_{50}$ (half-maximal inhibitory concentration)<50 nM.

We claim:

1. A crystalline Form 1 of of (S)-4-methyl-5-((4-((2-(methylamino)-6-(2,2,2-trifluoroethyl)thieno[2,3-d]pyrimidin-4-yl)amino)piperidin-1-yl)methyl)-1-(2-(4-(methylsulfonyl)piperazin-1-yl)propyl)-1H-indole-2-carbonitrile having an X-ray powder diffraction (XRPD) pattern with at least three characteristic peaks selected from 4.1° 2-Theta, 5.4° 2-Theta, 6.6° 2-Theta, 8.2° 2-Theta, 9.5° 2-Theta, 12.3° 2-Theta, 13.1° 2-Theta, 13.9° 2-Theta, 15.9° 2-Theta, 16.4° 2-Theta, 17.0° 2-Theta, 17.5° 2-Theta, 19.7° 2-Theta, and 22.6° 2-Theta.

2. A crystalline Form 1 of (S)-4-methyl-5-((4-((2-(methylamino)-6-(2,2,2-trifluoroethyl) thieno [2,3-d]pyrimidin-4-yl) amino) piperidin-1-yl) methyl)-1-(2-(4-(methylsulfonyl) piperazin-1-yl) propyl)-1H-indole-2-carbonitrile having an X-ray powder diffraction (XRPD) pattern set forth in FIG. 1.

3. The crystalline Form 1 of claim 1, wherein the crystalline form has an XRPD pattern with at least five characteristic peaks selected from 4.1° 2-Theta, 5.4° 2-Theta, 6.6° 2-Theta, 8.2° 2-Theta, 9.5° 2-Theta, 12.3° 2-Theta, 13.1° 2-Theta, 13.9° 2-Theta, 15.9° 2-Theta, 16.4° 2-Theta, 17.0° 2-Theta, 17.5° 2-Theta, 19.7° 2-Theta, and 22.6° 2-Theta.

4. The crystalline Form 1 of claim 1, wherein the crystalline form has a DSC thermogram set forth in FIG. 2.

5. The crystalline Form 1 of claim 1, wherein the crystalline form has a DSC thermogram with an endotherm having an onset at about 136° C. and/or a peak at about 149° C.

6. The crystalline Form 1 of claim 1, wherein the crystalline form has a TGA curve set forth in FIG. 3.

7. A crystalline Form 2 of (S)-4-methyl-5-((4-((2-(methylamino)-6-(2,2,2-trifluoroethyl) thieno [2,3-d]pyrimidin-4-yl) amino) piperidin-1-yl) methyl)-1-(2-(4-(methylsulfonyl) piperazin-1-yl) propyl)-1H-indole-2-carbonitrile having:
(a) an X-ray powder diffraction (XRPD) pattern set forth in FIG. 4; or
(b) an XRPD pattern with at least three characteristic peaks selected from 3.8° 2-Theta, 5.6° 2-Theta, 6.4° 2-Theta, 7.1° 2-Theta, 8.8° 2-Theta, 9.9° 2-Theta, 11.9° 2-Theta, and 14.8° 2-Theta; or
(c) (a) and (b).

8. A crystalline Form 3 of (S)-4-methyl-5-((4-((2-(methylamino)-6-(2,2,2-trifluoroethyl) thieno [2,3-d]pyrimidin-4-yl) amino) piperidin-1-yl) methyl)-1-(2-(4-(methylsulfonyl) piperazin-1-yl) propyl)-1H-indole-2-carbonitrile having:
(a) an X-ray powder diffraction (XRPD) pattern set forth in FIG. 5; or
(b) an XRPD pattern with at least three characteristic peaks selected from 7.9° 2-Theta, 9.5° 2-Theta, 11.0° 2-Theta, 15.7° 2-Theta, 16.5° 2-Theta, 18.0° 2-Theta, 19.0° 2-Theta, and 21.9° 2-Theta; or
(c) (a) and (b).

9. The crystalline Form 3 of claim 8, wherein the crystalline form has an XRPD pattern with at least five characteristic peaks selected from 7.9° 2-Theta, 9.5° 2-Theta, 11.0° 2-Theta, 15.7° 2-Theta, 16.5° 2-Theta, 18.0° 2-Theta, 19.0° 2-Theta, and 21.9° 2-Theta.

10. The crystalline Form 3 of claim 8, wherein the crystalline form has a DSC thermogram set forth in FIG. 6A.

11. The crystalline Form 3 of claim 8, wherein the crystalline form has a DSC thermogram with an endotherm having an onset at about 117° C. and/or a peak at about 135° C.

12. The crystalline Form 3 of claim 8, wherein the crystalline form has a TGA curve set forth in FIG. 6B.

13. The crystalline Form 3 of claim 8, wherein the crystalline form is an ethanol solvate.

14. A crystalline Form 4 of (S)-4-methyl-5-((4-((2-(methylamino)-6-(2,2,2-trifluoroethyl) thieno [2,3-d]pyrimidin-4-yl) amino) piperidin-1-yl) methyl)-1-(2-(4-(methylsulfonyl) piperazin-1-yl) propyl)-1H-indole-2-carbonitrile having:
(a) an X-ray powder diffraction (XRPD) pattern set forth in FIG. 7; or
(b) an XRPD pattern with at least three characteristic peaks selected from 8.1° 2-Theta, 9.4° 2-Theta, 10.8° 2-Theta, 13.5° 2-Theta, 15.7° 2-Theta, 16.3° 2-Theta, 17.5° 2-Theta, 18.3° 2-Theta, 18.7° 2-Theta, 20.1° 2-Theta, 21.6° 2-Theta, 21.8° 2-Theta, 25.2° 2-Theta, and 25.7° 2-Theta; or
(c) (a) and (b).

15. The crystalline Form 4 of claim 14, wherein the crystalline form has an XRPD pattern with at least five characteristic peaks selected from 8.1° 2-Theta, 9.4° 2-Theta, 10.8° 2-Theta, 13.5° 2-Theta, 15.7° 2-Theta, 16.3° 2-Theta, 17.5° 2-Theta, 18.3° 2-Theta, 18.7° 2-Theta, 20.1° 2-Theta, 21.6° 2-Theta, 21.8° 2-Theta, 25.2° 2-Theta, and 25.7° 2-Theta.

16. The crystalline Form 4 of claim 14, wherein the crystalline form has a DSC thermogram set forth in FIG. 8.

17. The crystalline Form 4 of claim 14, wherein the crystalline form has a DSC thermogram with an endotherm having an onset at about 127° C. and/or a peak at about 138° C.

18. A crystalline Form 5 of (S)-4-methyl-5-((4-((2-(methylamino)-6-(2,2,2-trifluoroethyl) thieno [2,3-d]pyrimidin-4-yl) amino)piperidin-1-yl) methyl)-1-(2-(4-(methylsulfonyl) piperazin-1-yl) propyl)-1H-indole-2-carbonitrile having:
(a) an X-ray powder diffraction (XRPD) pattern set forth in FIG. 9; or
(b) an XRPD pattern with at least three characteristic peaks selected from 7.9° 2-Theta, 8.5° 2-Theta, 9.6° 2-Theta, 11.1° 2-Theta, 15.8° 2-Theta, 16.9° 2-Theta, 18.4° 2-Theta, 19.1° 2-Theta, 22.1° 2-Theta, 25.5° 2-Theta, and 27.4° 2-Theta; or
(c) (a) and (b).

19. The crystalline Form 5 of claim 18, wherein the crystalline form has an XRPD pattern with at least five characteristic peaks selected from 7.9° 2-Theta, 8.5°

2-Theta, 9.6° 2-Theta, 11.1° 2-Theta, 15.8° 2-Theta, 16.9° 2-Theta, 18.4° 2-Theta, 19.1° 2-Theta, 22.1° 2-Theta, 25.5° 2-Theta, and 27.4° 2-Theta.

20. The crystalline Form 5 of claim 18, wherein the crystalline form has a DSC thermogram set forth in FIG. 10.

21. The crystalline Form 5 of claim 18, wherein the crystalline form has a DSC thermogram with an endotherm having an onset at about 122° C. and/or a peak at about 132° C.

22. The crystalline Form 5 of claim 18, wherein the crystalline form has a DVS curve set forth in FIG. 11.

23. The crystalline Form 5 of claim 18, wherein the crystalline form is an anhydrate.

24. A pharmaceutical composition comprising a crystalline form of (S)-4-methyl-5-((4-((2-(methylamino)-6-(2,2,2-trifluoroethythieno [2,3-d]pyrimidin-4-y1) amino) piperidin-1-yl) methyl)-1-(2-(4-(methylsulfonyl) piperazin-1-yl) propyl)-1H-indole-2-carbonitrile, wherein the crystalline form is:
(a) a crystalline Form 1 having an X-ray powder diffraction (XRPD) pattern with at least three characteristic peaks selected from 4.1° 2-Theta, 5.4° 2-Theta, 6.6° 2-Theta, 8.2° 2-Theta, 9.5° 2-Theta, 12.3° 2-Theta, 13.1° 2-Theta, 13.9° 2-Theta, 15.9° 2-Theta, 16.4° 2-Theta, 17.0° 2-Theta, 17.5° 2-Theta, 19.7° 2-Theta, and 22.6° 2-Theta; or
(b) a crystalline Form 2 having an XRPD pattern with at least three characteristic peaks selected from 3.8° 2-Theta, 5.6° 2-Theta, 6.4° 2-Theta, 7.1° 2-Theta, 8.8° 2-Theta, 9.9° 2-Theta, 11.9° 2-Theta, and 14.8° 2-Theta; or
(c) a crystalline Form 3 having an XRPD pattern with at least three characteristic peaks selected from 7.9° 2-Theta, 9.5° 2-Theta, 11.0° 2-Theta, 15.7° 2-Theta, 16.5° 2-Theta, 18.0° 2-Theta, 19.0° 2-Theta, and 21.9° 2-Theta; or
(d) a crystalline Form 4 having an XRPD pattern with at least three characteristic peaks selected from 8.1° 2-Theta, 9.4° 2-Theta, 10.8° 2-Theta, 13.5° 2-Theta, 15.7° 2-Theta, 16.3° 2-Theta, 17.5° 2-Theta, 18.3° 2-Theta, 18.7° 2-Theta, 20.1° 2-Theta, 21.6° 2-Theta, 21.8° 2-Theta, 25.2° 2-Theta, and 25.7° 2-Theta; or
(e) a crystalline Form 5 having an XRPD pattern with at least three characteristic peaks selected from 7.9° 2-Theta, 8.5° 2-Theta, 9.6° 2-Theta, 11.1° 2-Theta, 15.8° 2-Theta, 16.9° 2-Theta, 18.4° 2-Theta, 19.1° 2-Theta, 22.1° 2-Theta, 25.5° 2-Theta, and 27.4° 2-Theta; or
(f) any combination thereof; and
a pharmaceutically acceptable excipient.

25. A method of treating a disease or condition characterized by the interaction of menin with MLL in a subject comprising administering to the subject a therapeutically effective amount of the crystalline Form 1 of claim 1, wherein the disease or condition comprises a hematologic malignancy, a solid tumor cancer, or diabetes.

26. The method of claim 25, wherein the hematological malignancy is leukemia, myelodysplastic syndrome, or myelodysplastic/myeloproliferative neoplasm.

27. The method of claim 26, wherein the leukemia is acute myeloid leukemia or acute lymphoblastic leukemia.

28. The method of claim 25, wherein the solid tumor cancer is prostate cancer, breast cancer, liver cancer, or brain tumor.

29. A crystalline Form 1 of (S)-4-methyl-5-((4-((2-(methylamino)-6-(2,2,2-trifluoroethyl) thieno [2,3-d] pyrimidin-4-yl) amino) piperidin-1-yl) methyl)-1-(2-(4-(methylsulfonyl) piperazin-1-yl) propyl)-1H-indole-2-carbonitrile having a DSC thermogram set forth in FIG. 2.

30. A crystalline Form 1 of (S)-4-methyl-5-((4-((2-(methylamino)-6-(2,2,2-trifluoroethyl) thieno [2,3-d] pyrimidin-4-yl) amino) piperidin-1-yl) methyl)-1-(2-(4-(methylsulfonyl) piperazin-1-yl) propyl)-1H-indole-2-carbonitrile having a DSC thermogram with an endotherm having an onset at about 136° C. and/or a peak at about 149° C.

31. The crystalline Form 1 of claim 1, wherein the crystalline form has a purity and the purity of the crystalline form is no less than about 95%.

32. A method of treating an acute myeloid leukemia (AML) or an acute lymphoblastic leukemia (ALL) in a subject comprising administering to the subject a therapeutically effective amount of a crystalline Form 1 of (S)-4-methyl-5-((4-((2-(methylamino)-6-(2,2,2-trifluoroethyl) thieno [2,3-d] pyrimidin-4-yl) amino) piperidin-1-yl) methyl)-1-(2-(4-(methylsulfonyl) piperazin-1-yl) propyl)-1H-indole-2-carbonitrile having an X-ray powder diffraction (XRPD) pattern with at least three characteristic peaks selected from 4.1° 2-Theta, 5.4° 2-Theta, 6.6° 2-Theta, 8.2° 2-Theta, 9.5° 2-Theta, 12.3° 2-Theta, 13.1° 2-Theta, 13.9° 2-Theta, 15.9° 2-Theta, 16.4° 2-Theta, 17.0° 2-Theta, 17.5° 2-Theta, 19.7° 2-Theta, and 22.6° 2-Theta.

33. The method of claim 32, wherein the AML is menin-dependent AML, KMT2A-rearranged AML, or NPM 1-mutant AML.

34. The method of claim 32, wherein the ALL is KMT2A-rearranged ALL.

35. The crystalline Form 1 of claim 1, wherein the crystalline form is an anhydrate.

* * * * *